US012805740B2

(12) United States Patent
Alzahrani et al.

(10) Patent No.: US 12,805,740 B2
(45) Date of Patent: Nov. 24, 2026

(54) GRAPHENE-BASED ELECTRODES FOR ELECTROENCEPHALOGRAM-BASED BRAIN COMPUTER INTERFACE SYSTEMS

(71) Applicant: Imam Abdulrahman Bin Faisal University, Dammam (SA)

(72) Inventors: Saleh I. Alzahrani, Dammam (SA); Jwaher M. Alghamdi, Dammam (SA); Fatimah Almomen, Dammam (SA); Jenna Almofeez, Dammam (SA); Munirah Altwaijri, Dammam (SA); Rahaf Alsubaie, Dammam (SA); Rola Alghamdi, Dammam (SA); Hissah A. Alqahtani, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 770 days.

(21) Appl. No.: 18/315,554

(22) Filed: May 11, 2023

(65) Prior Publication Data

US 2024/0374157 A1 Nov. 14, 2024

(51) Int. Cl.

| | |
|---|---|
| ***A61B 5/05*** | (2021.01) |
| ***A61B 5/369*** | (2021.01) |
| ***A61N 1/36*** | (2006.01) |

(52) U.S. Cl.

CPC .................. *A61B 5/05* (2013.01); *A61N 1/36* (2013.01); *A61B 5/369* (2021.01)

(58) Field of Classification Search

CPC ........... A61B 5/05; A61B 5/369; A61B 5/268; A61B 5/266; A61B 2562/125;

(Continued)

(56) References Cited

U.S. PATENT DOCUMENTS

| | | | | |
|---|---|---|---|---|
| 2018/0310855 A1* | 11/2018 | Connor | .................. | A61B 5/291 |
| 2023/0172468 A1* | 6/2023 | Kaplan | .................. | A61B 5/332 600/470 |

(Continued)

FOREIGN PATENT DOCUMENTS

| | | |
|---|---|---|
| CN | 105548313 A | 5/2016 |
| CN | 104473637 B | 4/2017 |

(Continued)

OTHER PUBLICATIONS

Wiench et al. ; Enhanced performance of pyrrolic N-doped reduced graphene oxide-modified glassy carbon electrodes for dopamine sensing ; Journal of Electroanalytical Chemistry, vol. 852 ; Nov. 1, 2019 ; Abstract Only ; 3 Pages.

(Continued)

*Primary Examiner* — Jennifer Robertson
*Assistant Examiner* — Elina Sohyun Jang
(74) *Attorney, Agent, or Firm* — Oblon, McClelland, Maier & Neustadt, L.L.P.

(57) ABSTRACT

A brain-computer interface (BCI) system that includes a cap having wired electrodes selected such as a graphene-based electrode and a reduced graphene oxide (rGO)-coated electrode; a data acquisition and processing unit; and a computing device. The cap is operatively connected to the data acquisition and processing unit via the wired electrodes. The computing device has a communications interface coupled to the data acquisition and processing unit. A method of recording and monitoring brain activities of a subject via the BCI system. A method of making the graphene-based electrode and the reduced graphene oxide (rGO)-coated electrode.

13 Claims, 24 Drawing Sheets

(58) Field of Classification Search
CPC ........ A61B 5/291; A61N 1/36; A61N 1/0456; A61N 1/0476; A61N 1/0484; A61N 1/36025
See application file for complete search history.

(56) References Cited

U.S. PATENT DOCUMENTS

| | | | | |
|---|---|---|---|---|
| 2024/0090814 | A1* | 3/2024 | Vitale, III | A61B 5/27 |
| 2024/0148302 | A1* | 5/2024 | Murphy | A61B 5/296 |

FOREIGN PATENT DOCUMENTS

| | | | |
|---|---|---|---|
| CN | 106191967 | B | 1/2019 |
| CN | 110436584 | A | 11/2019 |
| CN | 109453808 | B | 2/2022 |
| WO | 2022/087681 | A1 | 5/2022 |

OTHER PUBLICATIONS

Ji et al. ; A Universal Electrolyte Formulation for the Electrodeposition of Pristine Carbon and Polypyrrole Composites for Supercapacitors ; ACS Applied Materials and Interfaces 12(11) ; 2020 ; 48 Pages.

Feng et al. ; Preparation of Graphene Polypyrrole Composite Film via Electrodeposition for Supercapacitors ; IEEE Transactions on Nanotechnology, vol. 11, Issue 6 ; May 21, 2012 ; Abstract Only ; 3 Pages.

* cited by examiner

GRAPHENE-BASED ELECTRODES FOR ELECTROENCEPHALOGRAM-BASED BRAIN COMPUTER INTERFACE SYSTEMS

BACKGROUND

Technical Field

The present disclosure relates to a brain-computer interface system and more specifically to a brain-computer interface system for high-throughput neural sensing/stimulation communication.

Discussion of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Paralysis may be caused due to an accident or a medical condition that affects, completely or partially, a way in which the muscles and the nerves function, including locked-in syndrome (LIS) and amyotrophic lateral sclerosis (ALS). Unfortunately, people with these disabilities often do not receive the required support owing to the cost of treatment. The National Institute of Neurological Disorders and Stroke (NINDS) defines LIS as a rare neurological disease that may be caused by traumatic brain injuries, or diseases such as ALS. It causes complete paralysis of many voluntary muscles in the human body, except those muscles responsible for the control of the eye. People who suffer from paralysis are aware of their surroundings but may be unable to communicate verbally or move.

Brain computer interface (BCI) technology is known to allow people with such disabilities to use brain-based communication and control to act upon multiple devices in their environment by decoding real-time recorded brain signals into commands [See: J. R. Wolpaw, N. Birbaumer, D. J. McFarland, G. Pfurtscheller, and T. M. Vaughan, "Brain-computer interfaces for communication and Control"]. Brain-computer interface (BCI) systems are known to establish a direct communication pathway between brain neural sensors and/or stimulators and external communication devices allowing a bidirectional information flow for researching, mapping, assisting, augmenting, or repairing human cognitive or sensory-motor functions.

With advancement in BCI technology, an event-related potential (ERP) component P300 was of interest in BCI applications due to its large peak [See: R. van Dinteren, M. Arns, M. L. A. Jongsma, and R. P. C. Kessels, "Combined frontal and parietal P300 amplitudes indicate compensated cognitive processing across the lifespan," Frontiers in Aging Neuroscience]. A common P300-based application is a speller [See: C. Wang, C. Guan and H. Zhang, "P300 Brain-Computer Interface Design for Communication and Control Applications"]. ERPs are small voltages that are generated from the brain as an evoked reaction to an event or stimuli [See: S. Sur and V. Sinha, "Event-related potential: An overview," Industrial Psychiatry Journal]. The ERPs may be observed by averaging the EEG signal that is time-locked to an event, e.g., visual stimulus. ERPs can be differentiated based on their latency (time after stimulus is presented to peak amplitude), polarity, amplitude, and electrode placement.

Sutton et al. [See: S. Sutton, M. Braren, J. Zubin, and E. R. John, "Evoked-Potential Correlates of Stimulus Uncertainty," Science, vol. 150, no. 3700. American Association for the Advancement of Science (AAAS), pp. 1187-1188] discovered that by presenting visual or auditory stimuli, a difference in the positive deflection of the averaged signal with latency of around 300 ms (i.e., P300) occurred, which indicates that the latency of P300 varies and does not always occur around 300 ms.

Picton [See: T. W. Picton, "The P300 Wave of the Human Event-Related Potential," Journal of Clinical Neurophysiology, vol. 9, no. 4. Ovid Technologies (Wolters Kluwer Health), pp. 456-479] noted that a positive peak that occurs between 200 ms to a later time (400 ms to 800 m, if target was difficult to distinguish) is identified as P300 and latency varies due to several factors, including age and electrode placement (for example, electrodes placed at the frontal locations usually have shorter latency compared to other locations).

Ritter and Vaughn [See: W. Ritter and H. G. Vaughan Jr., "Averaged Evoked Responses in Vigilance and Discrimination: A Reassessment," Science, vol. 164, no. 3877. American Association for the Advancement of Science (AAAS), pp. 326-328] introduced the 'oddball paradigm' where two different stimuli (standard and target) are randomly presented to the subjects. The subjects were instructed to focus on the target stimuli by either counting or pressing a button when it appeared amongst the more frequent standard stimuli.

Farwell and Donchin [See: L. A. Farwell and E. Donchin, "Talking off the top of your head: Toward a mental prosthesis utilizing event-related brain potentials," Electroencephalography and Clinical Neurophysiology] tested the P300 speller using the oddball paradigm. A 6×6 matrix with 36 characters was proposed, with a flashing duration of 100 ms for subsequent rows and columns and a pause of 75 ms in-between. With rows and columns flashing randomly, subjects were instructed to focus on the desired character only. With a probability of 1.67% of target flashing, the P300 that was evoked by the less frequent stimuli was detected by the machine and translated into the desired character.

Salvaris et al. [See: M. S. Salvaris and F. Sepulveda, "Robustness of the Farwell & Donchin BCI protocol to visual stimulus parameter changes," 2007 29th Annual International Conference of the IEEE Engineering in Medicine and Biology Society, 2007, pp. 2528-2531] disclosed that the protocol [as discussed in Farwell and Donchin] showed slight improvements with visual modifications. However, Cinel et al. [See: C. Cinel, R. Poli, and C. Citi, "Possible sources of perceptual errors in p300-based speller paradigm"] suggested that the closeness of the target symbol with other non-target symbols may evoke potentials similar to a P300 response. Fazel-Rezai [See: R. Fazel-Rezai, "Human error in P300 speller paradigm for braincomputer interface] found that similar potentials may cause incorrect selection of undesired symbols and could decrease the overall accuracy of the speller.

Krusienski et al. [See: D. J. Krusienski et al., "A comparison of classification techniques for the P300 Speller," Journal of Neural Engineering, vol. 3, no. 4] conducted a study of five different (four linear and one non-linear) classification methods that are used for P300-based BCI. The experiment was done on subjects that suffered from motor and speech disabilities using the same paradigm proposed by Farwell and Donchin. The recorded data was filtered and separated into segments (epochs), down sampled and assigned to one of two possibility groups, target or non-target. After training the different classifiers, classification accuracies of each type were obtained and compared. It was found that the linear classifiers outperformed the non-linear, and despite adequate results, the complexity of using a non-linear classifier is not justified. Out of the linear classification methods, Fisher's linear discriminant analysis (LDA) and stepwise linear discriminant analysis (SWLDA) showed better performance.

In another comparative study, Patelia and Patel [See: V. Patelia and M. S. Patel "A Comparative Study of Classification Techniques for P300 Speller," International Journal of Innovative Technology and Exploring Engineering] compared between two classification methods, LDA and Support Vector Machine (SVM). By using the P300-based speller protocol, classifiers were compared, and both had 91% classification accuracy.

Relevant P300-based BCI spellers all follow the international 10-20 EEG placement. However, the number of electrodes differ. Alvarado-González et al. [See: M. Alvarado-González, E. Garduño, E. Bribiesca, O. Yáñez-Suárez and V. Medina-Bañuelos, "P300 Detection Based on EEG Shape Features"] suggested using the C4, Cz, Fz, Pz, PO7, PO8, and Oz electrodes because they are positioned in the regions that affect attention and memory. In another study [See: Krusienski, D., Sellers, E., McFarland, D., Vaughan, T. and Wolpaw, J., 2022. *Toward enhanced P*300 *speller performance*], it was noted that P300 related research typically uses Fz, Cz, Pz electrodes. However, by adding additional posterior electrodes, the accuracy of the classifier could be enhanced.

Research associated with the BCI systems are aimed to improve LIS patients' quality of life. However, there are many drawbacks to conventional BCI systems which include conventional electrodes. Although the conventional electrodes provide adequate results, using such electrodes over time causes degradation of signal as well as increased impedance [See: J. Górecka and P. Makiewicz, "The dependence of electrode impedance on the number of performed EEG Examinations," Sensors, vol. 19, no. 11, p. 2608, 2019]. Conventional electrodes use conductive gel which leads to issues during the acquisition of a signal, such as a variation in impedance and a degradation of the quality of the signal received over time, due to the drying out of the gel. The gels also possess low charge carrier density, which lowers conductivity and signal-to-noise ratio (SNR) [See: K. E. Mathewson, T. J. Harrison, and S. A. Kizuk, "High and dry? comparing active dry EEG electrodes to active and passive wet electrodes," Psychophysiology, vol. 54, no. 1, pp. 74-82, 2016].

Accordingly, it is one objective of the present disclosure to provide an efficient BCI system that implements an electrode fabricated using a conductive material, such as graphene. A second objective of the present disclosure is to describe a method of recording and monitoring brain activities of a subject via the BCI system. A third objective of the present disclosure is to describe a method of preparing the graphene-based electrode.

SUMMARY

In an exemplary embodiment, the present disclosure provides a brain-computer interface (BCI) system that includes a cap having a plurality of wired electrodes. In some embodiments, the plurality of wired electrodes contains at least one electrode selected from the group consisting of a graphene-based electrode and a reduced graphene oxide (rGO)-coated electrode. The BCI system also includes a data acquisition and processing unit, and a computing device. The cap is operatively connected to the data acquisition and processing unit via the plurality of wired electrodes, and the computing device has a communications interface coupled to the data acquisition and processing unit. The plurality of wired electrodes is configured to detect one or more electroencephalograph (EEG) signals from a plurality of brain areas of a subject wearing the cap. The data acquisition and processing unit is configured to characterize brain activities of the subject based on the one or more EEG signals transmitted from the plurality of wired electrodes, where each EEG signal corresponds to the brain activities of the subject.

In some embodiments, each electrode of the plurality of wired electrodes is in the shape of a flat racket having a circular head portion and a rectangular tail portion. In some embodiments, each electrode of the plurality of wired electrodes has an average thickness in a range of 0.1 mm to 2 mm. In some embodiments, each electrode of the plurality of wired electrodes is etched with a pattern of etchings, trenches or concaves in a repeating pattern In some embodiments, the circular head portion of each electrode has an average diameter in a range of 4 mm to 20 mm. In some embodiments, the circular head portion of each electrode has a repeating pattern of etched lines that are radially oriented and evenly spaced inside the circular head portion of the electrode.

In some embodiments, the rectangular tail portion of each electrode has an average length in a range of 3 mm to 15 mm, and an average width of 1 mm to 3 mm. In some embodiments, the rectangular tail portion of each electrode has a series of repeating lines that extend from one edge of the rectangular tail portion to the other edge of the rectangular tail portion perpendicular to the axis of the rectangular tail portion.

In some embodiments, the data acquisition and processing unit includes a biosensing board and a dongle. In some embodiments, the biosensing board includes a processor and a neural interface having a plurality of channels. In some embodiments, the plurality of channels of the neural interface includes Pz, P4, Cz, C4, and Fz. In some embodiments, each electrode of the plurality of the wired electrodes is operatively connected to each channel of the plurality of channels of the neural interface.

In another exemplary embodiment, the present disclosure provides a method of recording and monitoring the brain activities of a subject via the BCI system. The method includes displaying one or more characters corresponding to an Arabic spelling by a computing device located in front of the subject wearing the cap of the BCI system, thereby generating one or more EEG signals from the subject's brain, where each electrode of the plurality of wired electrodes is operatively mounted on one or more regions of the subject's head. The method also includes receiving, via the plurality of wired electrodes of the cap, the one or more EEG signals corresponding to the brain activities of the subject, where each EEG signal of the one or more EEG signals is registered by one channel of a plurality of channels on a neural interface of the data acquisition and processing unit of the BCI system. The method also includes transmitting, via the plurality of channels, the one or more EEG signals to a processor of the data acquisition and processing unit and classifying the one or more EEG signals corresponding to the brain activities using one or more classification algorithms and generating a training data set. The method also includes analyzing the one or more EEG signals corresponding to the brain activities based on the training data set and generating one or more control signals based on the brain activities for computing device to record one or more characters in Arabic from the display in front of the subject.

In some embodiments, the classification algorithms classify the one or more EEG signals into target waveforms and non-target waveforms. In some embodiments, the one or more EEG signals has an amplitude of 0.1 to 5 microvolts (μV).

In some embodiments, the one or more regions on the subject's head comprise a parietal region, a central region, and a frontal region.

In some embodiments, the at least one electrode is a graphene-based electrode. In an aspect, the graphene-based electrode may be prepared by mixing and dissolving a surfactant in water to form a first solution, dispersing particles of a graphene-based material in the first solution to form a first suspension, mixing at least one acid with the suspension to form an acidified suspension, mixing pyrrole monomers with the acidified suspension to form an electrolyte composition, immersing a conductive substrate into the electrolyte composition and electrochemically coating the conductive substrate with a graphene-pyrrole polymer formed from the electrolyte composition, and removing the conductive substrate after the coating from the electrolyte composition, washing and drying to form the graphene-based electrode. In some embodiments, the graphene-based electrode has a signal-to-noise ratio (SNR) in a range of 1.8 to 2.0, and a specification of ISO/TR 19733:2019.

In some embodiments, the graphene-based electrode include at least one material selected from a group consisting of graphene, graphyne, graphydiyne, graphene oxide (GO), reduced graphene oxide (rGO), and exfoliated graphite. In some embodiments, the graphene-based material is present in the first suspension at a concentration of 5 to 600 mg/mL based on a total volume of the first solution.

In some embodiments, the surfactant includes an alkyl sulfate surfactant having a formula of $ROSO_3^-M^+$, where R is a linear C8-C20 hydrocarbyl group, M is an alkali metal, and the surfactant is present in the first solution at a concentration of 0.03 to 0.3 molar (M).

In some embodiments, the at least one acid is selected from a group consisting of hydrochloric acid, sulfuric acid, perchloric acid, and nitric acid.

In some embodiments, the pyrrole monomers are present in the electrolyte composition at a concentration of 5 to 60 mg/mL based on a total volume of the first solution.

In some embodiments, the conductive substrate is an indium tin oxide (ITO) coated polymer substrate, and wherein the polymer substrate comprises at least one polymer selected from the group consisting of polyethylene terephthalate (PET), polyacetylene, polyphenylene vinylene, polythiophene, polyaniline, and polyphenylene sulfide.

In some embodiments, the at least one electrode is a reduced graphene oxide (rGO)-coated electrode. In an aspect, the reduced graphene oxide (rGO)-coated electrode may be prepared by dispersing rGO particles in a liquid to form a second suspension, and dip coating a conductive substrate in the second suspension and drying to form the rGO-coated electrode having a layer of the RGO particles at least partially covered on a surface of the conductive substrate, where the rGO-coated electrode has a specification of ISO/TR 19733:2019.

In some embodiments, the liquid is at least one selected from a group consisting of a hydrochloric acid solution, dimethylformamide, and a combination thereof.

According to the present disclosure, the graphene-based electrode addresses the issues discussed earlier with respect to the conventional electrodes. Electron mobility, high surface area, and electrical conductivity are profound characteristics of graphene. Graphene based electrodes also provides an ease of communication by enhancing the signal obtained thereby to produce a greater signal with an increased SNR, and an improved contact impedance. The fabricated graphene electrodes are intended to collect an electroencephalogram (EEG) signal with an improved SNR which enhances the performance of the P300 Arabic speller based BCI system. By obtaining the EEG signals through graphene electrodes, patients with neuromuscular diseases are provided with a communication and control channel through P300 Arabic Speller.

These and other aspects of non-limiting embodiments of the present disclosure will become apparent to those skilled in the art upon review of the following description of specific non-limiting embodiments of the disclosure in conjunction with the accompanying drawings.

BRIEF DESCRIPTION OF THE DRAWINGS

A better understanding of embodiments of the present disclosure (including alternatives and/or variations thereof) may be obtained with reference to the detailed description of the embodiments along with the following drawings, in which.

DETAILED DESCRIPTION

Figure 1:
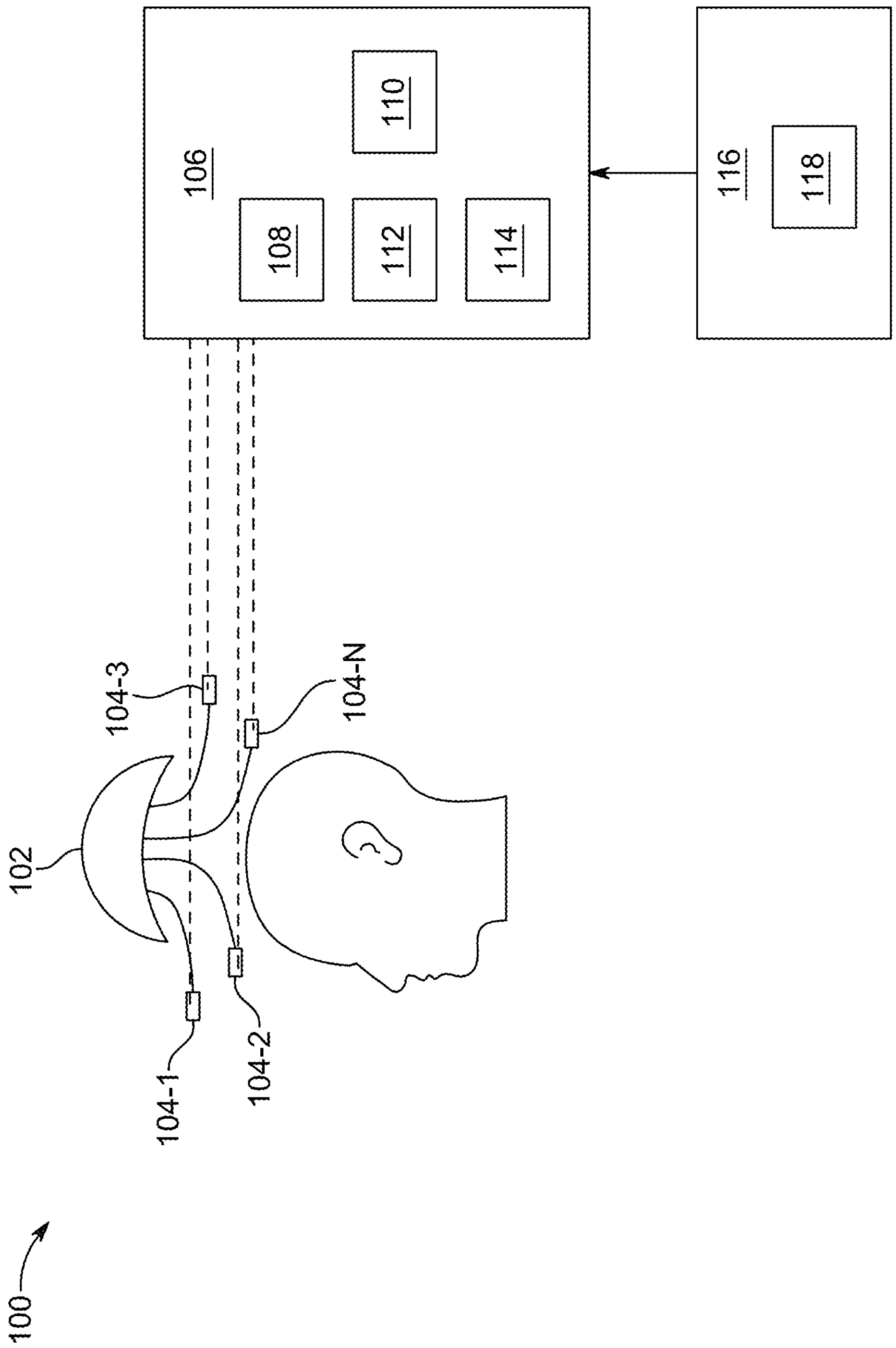
FIG. 1 illustrates an exemplary diagram of a brain-computer interface (BCI) system, according to an aspect of the present disclosure.

In the following description, it is understood that other embodiments may be utilized, and structural and operational changes may be made without departure from the scope of the present embodiments disclosed herein.

Reference will now be made in detail to specific embodiments or features, examples of which are illustrated in the accompanying drawings. Wherever possible, corresponding, or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

In the drawings, like reference numerals designate identical or corresponding parts throughout the several views. Further, as used herein, the words “a,” “an” and the like generally carry a meaning of “one or more,” unless stated otherwise.

Furthermore, the terms “approximately,” “approximate,” “about,” and similar terms generally refer to ranges that include the identified value within a margin of 20%, 10%, or preferably 5%, and any values therebetween.

Graphene, although a strong material, can still be prone to breakage. Therefore, to enhance its performance and durability, it may be combined with other materials. Graphene exhibits high surface-to-volume ratio, tensile strength, high thermal and electrical conductivity, as well as affordability, and therefore may be preferred over conventional carbon nanotubes. With technological improvements, it is possible to modify graphene and its derivatives (GO, rGO) with polymers to develop graphene-polymer composite materials.

Aspects of the present disclosure relate to a brain-computer interface (BCI) system and a method of recording and monitoring brain activities of a subject via the BCI system. Patients with diseases that damage their neuromuscular pathways, such as amyotrophic lateral sclerosis, may suffer from paralysis. In severe cases, the patients may suffer from locked-in syndrome, a total loss of voluntary muscle control that prohibits their communication, while the brain still functions. A P300 speller is one of brain-computer interface applications that allows for such patients to communicate with others using their thoughts. In the present disclosure, an Arabic P300-based speller is disclosed, where an offline analysis was conducted using channels (Pz, P4, Cz, C4, Fz) to test the functionality of fabricated electrode. Graphene material has been in the study in many areas due to its high conductivity and stability in different temperatures. The BCI system implements a fabricated graphene-based electrode to address limitations of Ag/AgCl electrodes. To do so, an electrode shaped PET was used as a substrate in electrochemical deposition in a solution of graphene-pyrrole. A resultant electrode was compared to a conventional electrode with regard to signal acquisition. Since the conventional electrodes are sensitive to motion artifacts and the available graphene electrodes are susceptible to breakage due to its brittleness, the present disclosure describes experiments conducted to find an optimum method and structure that improves the flexibility of the graphene electrode and SNR compared with the conventional electrodes.

FIG. 1 illustrates an exemplary diagram of a brain-computer interface (BCI) system 100, according to an embodiment of the present disclosure. The system 100 includes a cap 102 having a plurality of wired electrodes 104-1, 104-2, 104-3, . . . , 104-N (hereinafter collectively and commonly referred to as "the wired electrodes 104"). The cap 102 may be made from a flexible material and may be adapted to be worn on a head of a subject, such as a patient. In some embodiments, the cap 102 may be adapted to house a power source, such as a battery (not shown) to power the wired electrodes 104. As illustrated in FIG. 1, wires of the wired electrodes 104 extend from an inner surface of the cap 102, where ends of such wires may be connected to the battery. The wired electrodes 104 include at least one electrode selected from a group consisting of a graphene-based electrode and a reduced graphene oxide (rGO)-coated electrode. The wired electrodes 104 are configured to detect one or more electroencephalograph (EEG) signals from a plurality of brain areas of the subject wearing the cap 102.

The system 100 further includes a data acquisition and processing unit 106, where the cap 102 is operatively connected to the data acquisition and processing unit 106 via the plurality of wired electrodes 104. As used herein, the term "operatively connected" refers to a transfer of inputs from the wired electrodes 104 to the data acquisition and processing unit 106, and vice-versa. The data acquisition and processing unit 106 is configured to characterize brain activities of the subject based on the one or more EEG signals transmitted from the plurality of wired electrodes 104, where each EEG signal of the one or more EEG signals corresponds to the brain activities of the subject. In some embodiments, the data acquisition and processing unit 106 includes a biosensing board 108 and a dongle 110. The biosensing board 108 includes a processor 112 and a neural interface 114 having a plurality of channels (for example, EEG simulation channels), namely Pz, P4, Cz, C4 and Fz. Each electrode of the plurality of the wired electrodes 104 is operatively connected to one channel of the plurality of channels of the neural interface 114.

The system 100 also includes a computing device 116 having a communications interface 118 coupled to the data acquisition and processing unit 106. The system 100 removably retains the computing device 116.

Figure 7A:
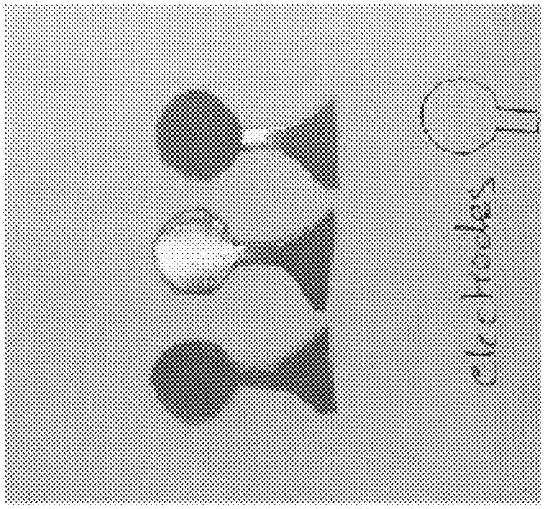
FIG. 7A illustrates PET electrodes, according to an aspect of the present disclosure.

Referring to FIG. 7A, a PET electrode, and FIGS. 23A to D, a CAD drawing of the graphene-based electrode. Each electrode of the plurality of wired electrodes is in the shape of a flat racket having a circular head portion and a rectangular tail portion. In some embodiments, the electrode has an average thickness in a range of 0.1 to 2 millimeters (mm), preferably 0.3 to 1.8 mm, preferably 0.5 to 1.5 mm, preferably 0.8 to 1.3 mm, or even more preferably about 1 mm. In some further embodiments, the circular head portion of each electrode has an average diameter in a range of 4 to 20 mm, preferably 6 to 18 mm, preferably 8 to 16 mm, preferably 10 to 14 mm, or even more preferably about 12 mm. In some more preferred embodiments, the rectangular tail portion of each electrode has an average length in a range of 3 to 15 mm, preferably 5 to 13 mm, preferably 7 to 11 mm, or even more preferably about 9 mm. In some most preferred embodiments, the rectangular tail portion of each electrode has an average width of 1 to 3 mm, preferably 1.5 to 2.5 mm, or even more preferably about 2 mm. Other ranges are also possible.

In a preferred embodiment of the invention, the electrode, such as a PET film, is etched or embossed with a pattern of etchings, trenches or concaves in a repeating pattern. The pattern along the tab portion (also referred to herein as "rectangular tail portion") of the electrode is preferably a series of repeating lines that extend from one edge of the tab portion to the other edge of the tab portion perpendicular to the axis of the tab. The repeated etchings or concaves preferably have a width that is 1/10 or less the width of the tab a portion of the electrode, preferably a width of 0.05-0.2 mm, preferably about 0.1 mm.

Figure 23A:
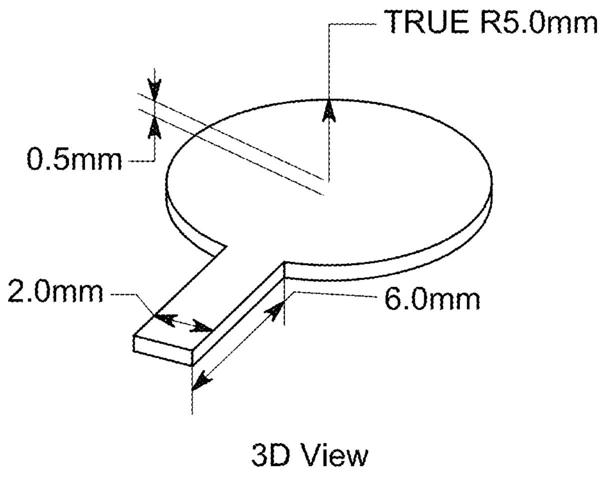
FIG. 23A is a perspective view of a CAD drawing of the graphene-based electrode, according to an aspect of the present disclosure.
Figure 23B:
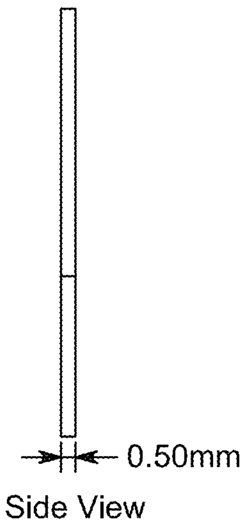
FIG. 23B is a side view of a CAD drawing of the graphene-based electrode, according to an aspect of the present disclosure.
Figure 23C:
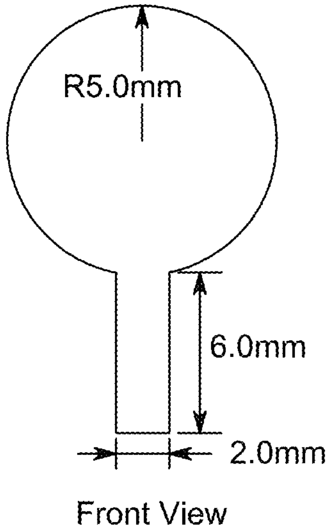
FIG. 23C is a front view of a CAD drawing of the graphene-based electrode, according to an aspect of the present disclosure.
Figure 23D:
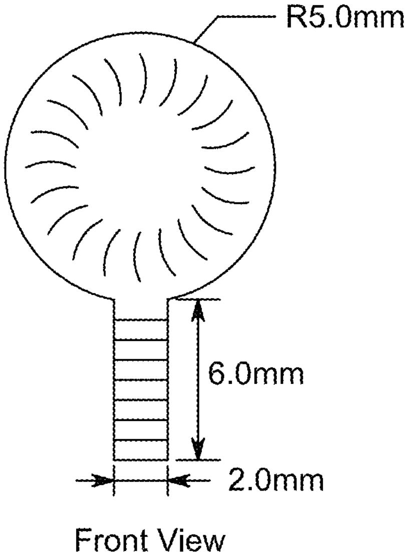
FIG. 23D is a front view of a CAD drawing illustrating the graphene-based electrode with repeating pattern of etched lines, according to an aspect of the present disclosure.

The etchings or concaves in the circular head portion of the electrode are radially oriented and have a length that is approximately the same as the length of the etchings on the tab portion of the electrode, for example a length of 0.5-2 mm, preferably about 1 mm. The etchings or concaves are evenly spaced inside the circumference of the electrode and may be in the form of straight lines or arcs. Repeating nested radial markings such as those shown in FIG. 23D are preferred. Preferably 2-4 concentric rings of etchings, trenches or concaves are present in the head portion of the electrode. The etchings and/or concaves provide better contact between the graphene and/or graphene oxide coating and the underlying film. The etchings or concaves impart a greater degree of flexibility to the electrode with a reduced risk of delamination or detachment from the underlying film. The etchings and/or concaves can be added to the film prior to coating with graphene and/or graphene oxide using a number of techniques such as laser etching, pressure embossing or mechanical surface planning.

In some embodiments, the data acquisition and processing unit 106 comprises a biosensing board 108 and a dongle 110. In some embodiments, the biosensing board 108 comprises a processor 112 and a neural interface 114 having a plurality of channels. In some further embodiments, each electrode of the plurality of the wired electrodes 104 is operatively connected to one channel of the plurality of channels of the neural interface 114. In some preferred embodiments, the plurality of channels of the neural interface 114 comprise Pz, P4, Cz, C4 and Fz.

Figure 12B:
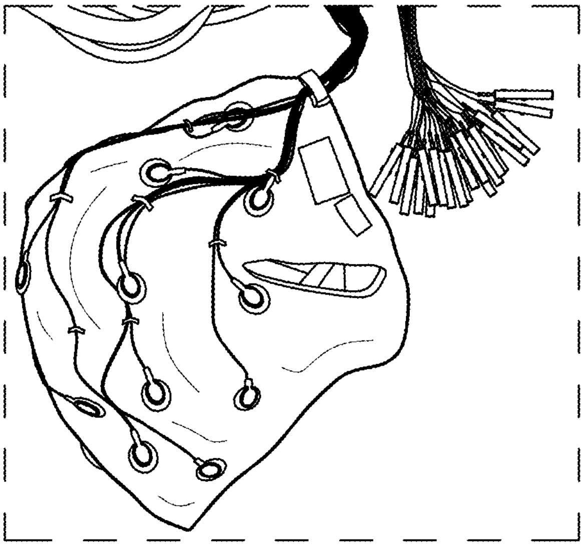
FIG. 12B illustrates EEG Electrode Cap Kit from OpenBCI with the 10-20 electrodes placement system, according to an aspect of the present disclosure.
Figure 12A:
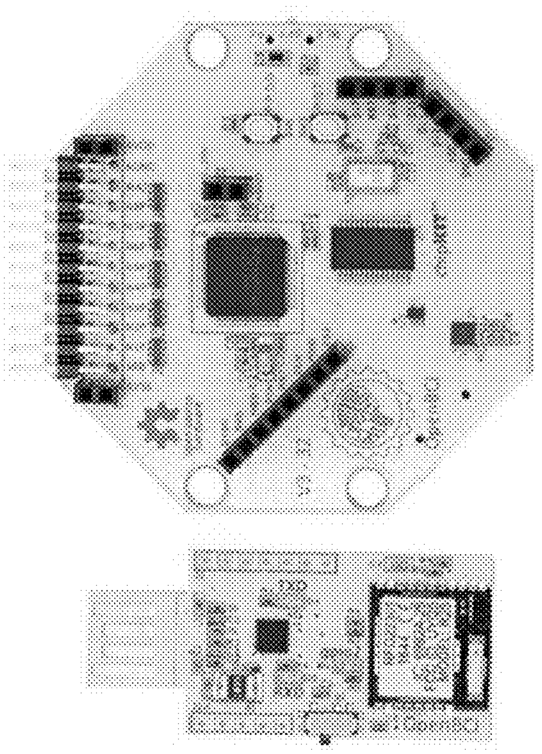
FIG. 12A illustrates an OpenBCI Cyton board and dongle used in an experiment described in the present disclosure.

Referring to FIG. 12A and B, in some embodiments, the biosensing board 108 may be an OpenBCI Cyton Biosensing Board having 8-channel neural interface 114 with a 32-bit processor 112. In some embodiment, the OpenBCI Cyton Biosensing board 108 may be connected via OpenViBE Acquisition Server where the driver was chosen as OpenBCI with modified index. In some further embodiment, OpenBCI GUI v5.0.8 was used to acquire and process data. OpenViBE Designer v3.1.0 was used to create scenarios for data acquisition and feature extraction. Each electrode of the plurality of the wired electrodes 104-1, 104-2, 104-3, . . . , 104-N is operatively connected to each channel of the 8-channel neural interface 114.

Figure 8:
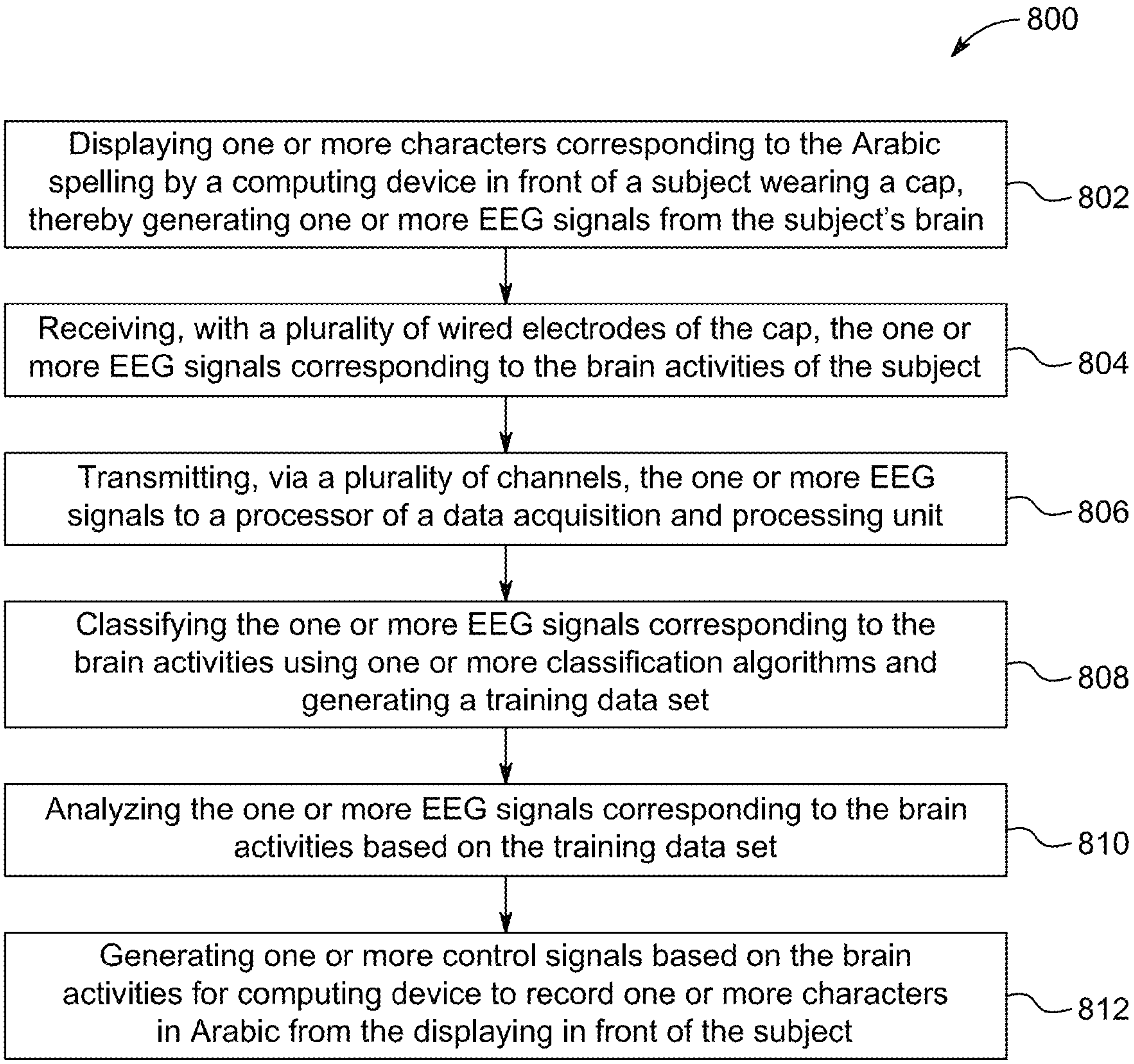
FIG. 8 is a flowchart of a method of recording and monitoring brain activities of a subject via the BCI system, according to an aspect of the present disclosure.

FIG. 8 is a flowchart of a method 800 of recording and monitoring brain activities of a subject via the system 100. At step 802, the method 800 includes displaying one or more characters corresponding to the Arabic spelling by the computing device 116 (see FIG. 1) in front of the subject wearing the cap thereby generating one or more EEG signals from the subject's brain. Each electrode of the plurality of wired electrodes is operatively mounted on one or more regions of the subject's head. The one or more regions on the subject's head comprise a parietal region, a central region, and a frontal region. In some embodiments, the subjects was seated 0.2 to 2 meters (m), preferably 0.4 to 1 m, or even more preferably about 0.6 m from a 12 to 85-inch screen, preferably 18 to 55-inch screen, or even more preferably about 27-inch screen while instructed to no move or blink unnecessarily. The original speller visualizer had a 6×6 matrix containing English characters that was then converted to Arabic letters. In some embodiments, the background of the speller was set to black, while the letters were grey until they flashed in white. In some further embodiments, the subject completed the experiment used the Arabic speller. In some further embodiments, the session started within 60 s, preferably within 40 s, or even more preferably within 20 s as a pre-rest then the first target character is flashed in blue with a duration of 500 to 2000 ms, preferably 800 to 1500 ms, or even more preferably about 1000 ms for the subject to focus on. In some preferred embodiments, a single repetition had an inter-repetition-delay of 0.5 to 5 s, or more preferably about 1 s, allowing the user to rest. The flashes were intensified for 50 to 500 ms, preferably 150 to 350 ms, or even more preferably about 200 ms with an inter-stimulus-interval (ISI) of 50 to 200 ms, or more preferably about 100 ms. A rest duration of 1 to 10 s, or more preferably about 3 s between each target character was employed. To further evoke the P300 signal, the participants (subjects) were asked to count the number of times the desired character flashed. Other ranges are also possible. In some embodiments, the one or more regions on the subject's head comprise a parietal region, a central region, and a frontal region.

At step 804, the method 800 includes receiving, with the plurality of wired electrodes of the cap, the one or more EEG signals corresponding to the brain activities of the subject. Each EEG signal of the one or more EEG signals is registered by one channel of a plurality of channels on a neural interface of the data acquisition and processing unit 106 (see FIG. 1)

At step 806, the method 800 includes transmitting, via the plurality of channels, the one or more EEG signals to a processor of the data acquisition and processing unit 106. In some embodiments, each of Ag/AgCl EEG electrode was placed on the parietal, center, and frontal regions via (Pz, P4, Cz, C4, Fz) channels. In some embodiments, the impedance of the electrodes for all subjects was kept under 30 kiloohms (kΩ), preferably under 20 kΩ, or even more preferably under 10 kΩ. In some further embodiments, the OpenBCI had a band-pass filter of 1 to 100 Hz, or more preferably 5-50 Hz, and a band-reject filter that eliminates the noise at 20 to 100 Hz, preferably 40 to 80 Hz, or even more preferably about 60 Hz in Saudi Arabian powerlines. In some preferred embodiments, the obtained EEG signals were stored in. .OV format and filtered by a 4th-order Butterworth band-pass filter to reject any signals outside the band 1 to 100 Hz, or more preferably 1-20 Hz. A pass-band ripple of 0.1 to 2 dB, or more preferably about 0.5 dB was set to account for the variation in the amplitude within the designated filter.

At step 808, the method 800 includes classifying the one or more EEG signals corresponding to the brain activities using one or more classification algorithms and generating a training data set. The classification algorithms classify the one or more EEG signals into target waveforms and non-target waveforms.

At step 810, the method 800 includes analyzing the one or more EEG signals corresponding to the brain activities based on the training data set.

Figure 21:
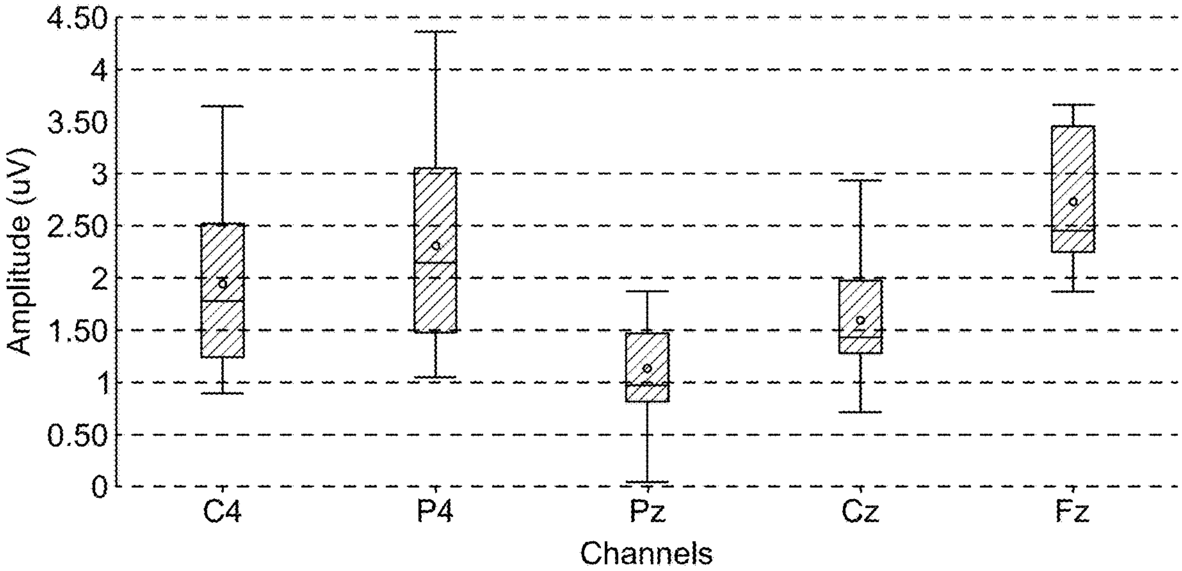
FIG. 21 illustrates box plot illustrating a relationship between the channels and their respective amplitude, according to an aspect of the present disclosure.

At step 812, the method 800 includes generating one or more control signals based on the brain activities for computing device to record one or more characters in Arabic from the displaying in front of the subject. Referring to FIG. 21, a box plot illustrating a relationship between the channels and their respective amplitude. In some embodiments, the method has an amplitude of 0.1 to 5 microvolts (μV). In some embodiments, the C4 channel has an amplitude of 0.8 to 4 μV, preferably 1.5 to 3 μV, or even more preferably 2 to 2.5 μV. In some embodiments, the P4 channel has an amplitude of 1 to 4.5 μV, preferably 2 to 3.5 μV, or even more preferably 2.5 to 3 μV. In some embodiments, the Pz channel has an amplitude of 0.1 to 2 μV, preferably 0.5 to 1.5 μV, or even more preferably about 1 μV. In some embodiments, the Cz channel has an amplitude of 0.5 to 3 μV, preferably 1 to 2 μV, or even more preferably about 2.5 μV. In some embodiments, the Fz channel has an amplitude of 1.5 to 4 μV, preferably 2 to 3 μV, or even more preferably about 2.5 μV. Other ranges are also possible.

In an embodiment, the electrode is a graphene-based electrode which is prepared by mixing and dissolving a surfactant in water to form a first solution. In some embodiment, the surfactant may include an alkyl sulfate surfactant having a formula of $ROSO_3^-M^+$, wherein R is a linear C8-C20 hydrocarbyl group, and wherein M is an alkali metal. In some embodiments, the surfactant is sodium dodecyl sulfate (SDS). In some further embodiments, the surfactant is present in the first solution at a concentration of 0.03 to 0.3 molar (M), preferably 0.1 to 0.25 M, or even more preferably about 0.2 M. Other ranges are also possible.

The method of preparing the graphene-based electrode further includes steps of dispersing particles of a graphene-based material in the first solution to form a first suspension and mixing at least one acid with the suspension to form an acidified suspension. In some embodiments, the graphene-based material is present in the first suspension at a concentration of 5 to 600 mg/mL based on a total volume of the first solution, preferably 100 to 500 mg/mL, preferably 200 to 400 mg/mL, or even more preferably about 300 mg/mL. Other ranges are also possible. In some embodiment, the at least one acid is selected from the group consisting of hydrochloric acid, sulfuric acid, perchloric acid, and nitric acid. In some embodiments, the acidified suspension has a pH of less than 8, preferably less than 6, or even more preferably less than 4. Other ranges are also possible.

The method of preparing the graphene-based electrode further includes steps of mixing pyrrole monomers with the acidified suspension to form an electrolyte composition. In some embodiment, the pyrrole monomers are present in the electrolyte composition at a concentration of 5 to 60 mg/mL based on a total volume of the first solution, preferably 10 to 50 mg/mL, preferably 20 to 40 mg/mL, or even more preferably about 30 mg/mL. Other ranges are also possible. The method further includes immersing a conductive substrate into the electrolyte composition and electrochemically coating the conductive substrate with a graphene-pyrrole polymer formed from the electrolyte composition. In some embodiments, the conductive substrate includes a glass portion, and a polymer portion. In some embodiments, the glass portion is in the form of a coating layer at least partially covering a surface of the polymer portion. In some further embodiments, the polymer portion is at least 50% covered by the glass portion based on a total surface area of the polymer portion, preferably at least 70%, preferably at least 90%, or even more preferably at least 99% based on the total surface area of the polymer portion. In some preferred embodiments, the glass portion of the conductive substrate is at least one selected from the group consisting of a fluorine-doped tin oxide (FTO) glass, a tin-doped indium oxide (ITO) glass, an aluminum doped zinc oxide (AZO) glass, a niobium doped titanium dioxide (NTO) glass, an indium doped cadmium oxide (ICO) glass, an indium doped zinc oxide (IZO) glass, a fluorine doped zinc oxide (FZO) glass, a gallium doped zinc oxide (GZO) glass, an antimony doped tin oxide (ATO) glass, a phosphorus-doped tin oxide (PTO) glass, a zinc antimonate glass, a zinc oxide glass, a ruthenium oxide glass, a rhenium oxide glass, a silver oxide glass, and a nickel oxide glass. In some embodiments, the conductive substrate is an indium tin oxide (ITO) polymer substrate, and the polymer substrate includes at least one polymer selected from the group consisting of polyethylene terephthalate (PET), polyacetylene, polyphenylene vinylene, polythiophene, polyaniline, and polyphenylene sulfide. In some most preferred embodiments, the polymer substrate is polyethylene terephthalate (PET).

As used herein, the term "electrochemical cell" refers to a device capable of either generating electrical energy from chemical reactions or using electrical energy to cause chemical reactions.

Figure 7B:
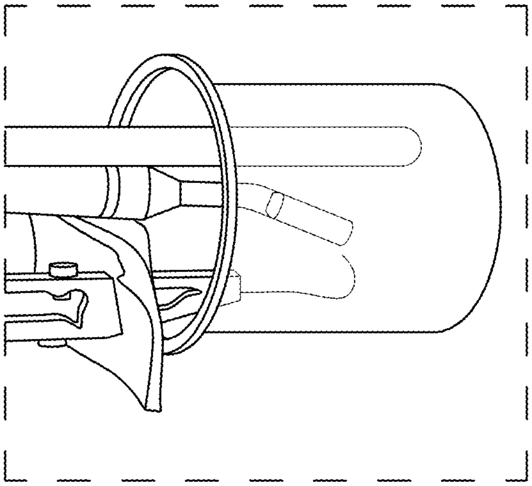
FIG. 7B illustrates preparation of cell, according to an aspect of the present disclosure.
Figure 7C:
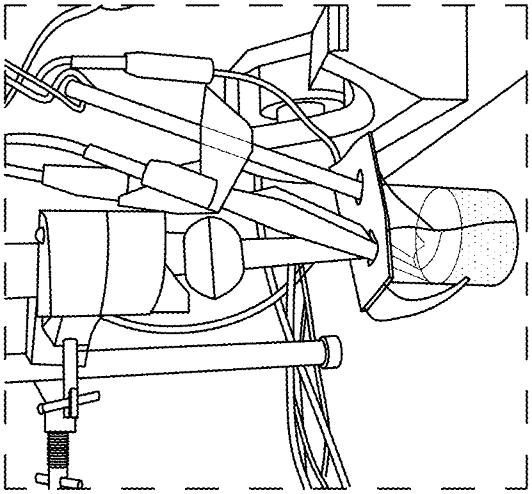
FIG. 7C illustrates polymerization setup, according to an aspect of the present disclosure.

The electrochemical coating may be performed in a 3-electrode electrochemical cell equipped with a chemical station for evaluating the performance of the electrode. In some embodiments, the cell may also include an Ag/AgCl (KCl solution of 3.0 M) reference electrode, a graphite counter electrode, and a working electrode. In some embodiments, the working electrode may be ITO coated PET substrate. In some further embodiment, reference electrode placed between the working electrode, holding the PET with the ITO side facing inwards, the counter electrode, holding the graphite rod, as depicted in FIG. 7B, and 7C. In some preferred embodiments, a linear sweep voltammetry test may be performed at a scan rate of 10 mV/s. In some further preferred embodiments, the Gamry Electrochemical Instrument was used for the polymerization process. The chronoamperometry technique was utilized with a voltage of 0.1 to 2 V, or more preferably about 0.9 V for at least 0.5 h, preferably at least 1h, or even more preferably at least 2 h for both the graphene-pyyrole containing and rGO-pyrrole containing solutions. Other ranges are also possible.

The method further includes removing the conductive substrate after the coating from the electrolyte composition, washing and drying to form the graphene-based electrode. The graphene-based electrode has a signal-to-noise ratio (SNR) in a range of 1.8 to 2.0, and a specification of ISO/TR 19733:2019. In some embodiments, the graphene-based material comprises at least one selected from the group consisting of graphene, graphyne, graphydiyne, graphene oxide (GO), reduced graphene oxide (rGO), and exfoliated graphite.

In some embodiment, the at least one electrode is a reduced graphene oxide (rGO)-coated electrode prepared by dispersing rGO particles in a liquid to form a second suspension and dip coating a conductive substrate in the second suspension and drying to form the rGO-coated electrode having a layer of the RGO particles at least partially covered on a surface of the conductive substrate, where the rGO-coated electrode has a specification of ISO/TR 19733:2019. In some embodiment, the liquid is at least one selected from the group consisting of a hydrochloric acid solution, dimethylformamide, and a combination thereof.

In some embodiments, the rGO particles may be present in the second suspension at a concentration of 5 to 600 mg/mL based on a total volume of the second suspension, preferably 100 to 500 mg/mL, preferably 200 to 400 mg/mL, or even more preferably about 300 mg/mL based on the total volume of the second suspension. Other ranges are also possible.

In some embodiments, The method further includes preparing a rGo from graphene by dispersing graphene particles in ethanol and sonicating to form a third suspension; filtering the third suspension and drying to form activated graphene particles; dispersing the activated graphene particles in an acid mixture and heating to form GO particles; separating the GO particles from the acid mixture, washing and calcining at a temperature of 400 °C to form rGO particles. In some embodiments, the activated graphene particles are present in the acid mixture at a concentration of 0.1 to 1 mg/mL, preferably 0.3 to 0.8 mg/mL, or even more preferably about 0.6 mg/mL. In some further embodiments, the acid mixture contains sulfuric acid and nitric acid. In some preferred embodiments, a ratio of the sulfuric acid to the nitric acid in the acid mixture is in a range of 8:1 to 1:1, preferably 6:1 to 2:1, or even more preferably about 3:1. Other ranges are also possible.

EXAMPLES

The following examples describe and demonstrate exemplary embodiments of a BCI system containing a fabricated graphene-based electrode, and a method of preparing the graphene-based electrode, as described herein. The examples are provided solely for the purpose of illustration and are not to be construed as limitations of the present disclosure, as many variations thereof are possible without departing from the spirit and scope of the present disclosure.

Example 1: Experiments

The experiment included two methods to fabricate the graphene-based electrodes. The first method included processing the graphene paste by converting it to GO, rGO, followed by coating the 3D printed electrode with the graphene paste. The second method included fabrication of graphene-based electrodes through electrochemical deposition. Graphene and rGO were mixed with pyrrole monomer, which through polymerization rendered a conductive polymer, and was deposited on a PET sheet.

Figure 2B:
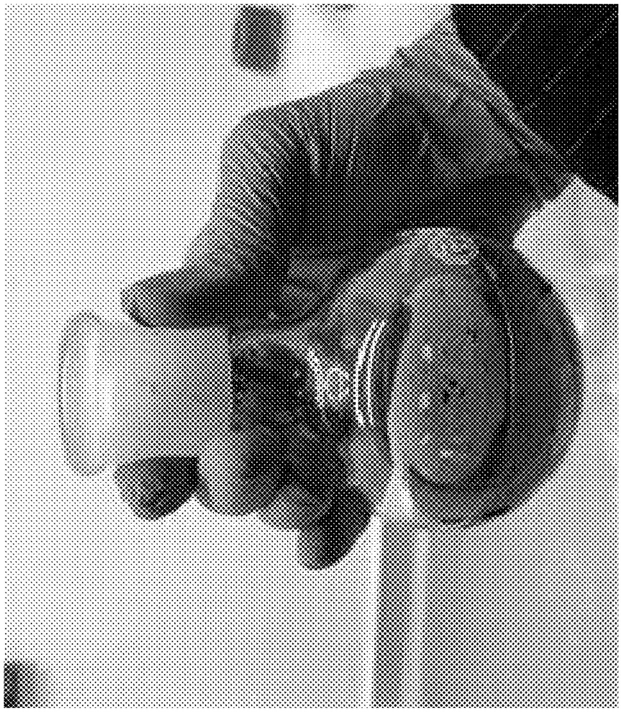
FIG. 2B illustrates graphene oxide (GO) solution preparation, according to an aspect of the present disclosure.
Figure 2A:
FIG. 2A illustrates extracted graphene powder, according to an aspect of the present disclosure.
Figure 2D:
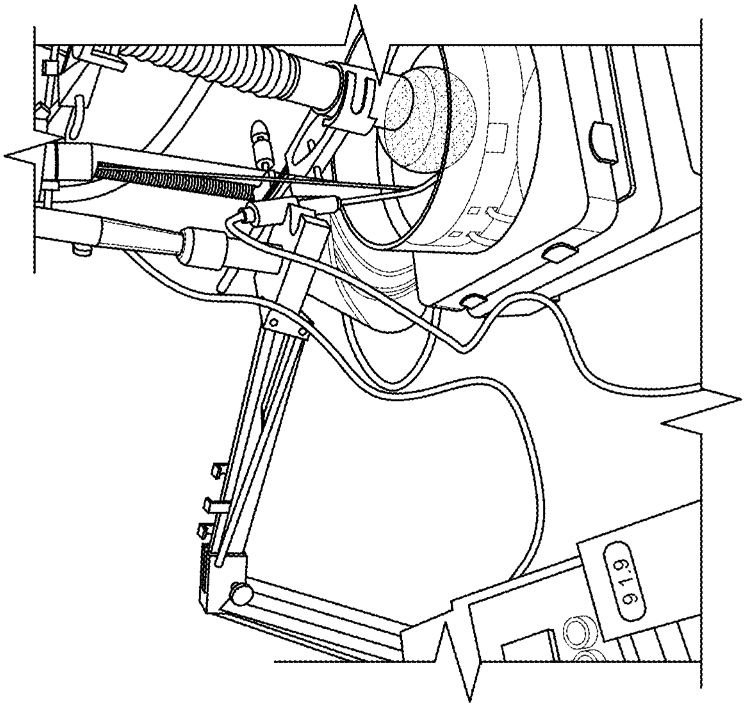
FIG. 2D illustrates the GO process, according to an aspect of the present disclosure.
Figure 2C:
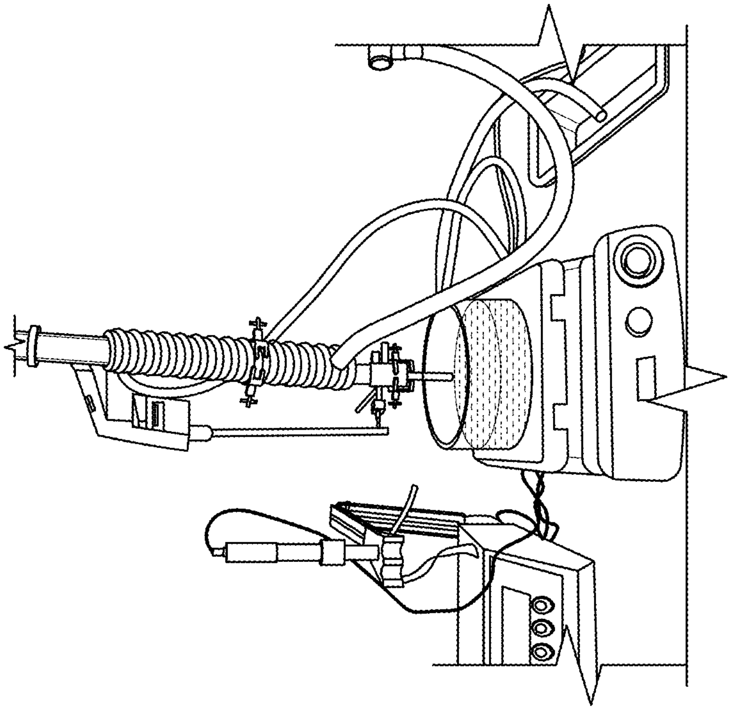
FIG. 2C illustrates GO experiment setup, according to an aspect of the present disclosure.

Referring to FIG. 2A, 0.5 g of graphene paste was mixed with 10 ml of ethanol and left in an ultrasonicator for 1.5 h. The mixture was then centrifuged at 2000 rpm for 3 min and again at 4000 rmp for 6 min. Subsequently, the mixture was filtered through filtering paper and finally left in the oven at 120 °C for 2 h. FIG. 2B illustrates the GO solution preparation where 50 mg of a resultant graphene powder was added to a flask containing 60 ml and 20 ml of sulfuric and nitric acids, respectively. FIG. 2C and FIG. 2D show the GO experimental setup. The oil bath's stirrer was set at 90 °C±10 and 600 rmp. A reflux condenser was attached to the flask and the experiment was left for 4 h.

Figure 3A:
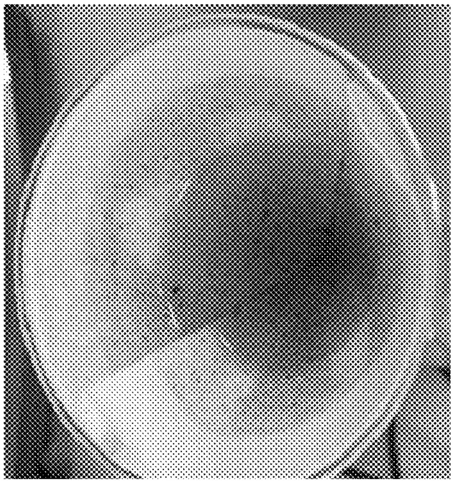
FIG. 3A illustrates a step of filtering GO solution, according to an aspect of the present disclosure.
Figure 3B:
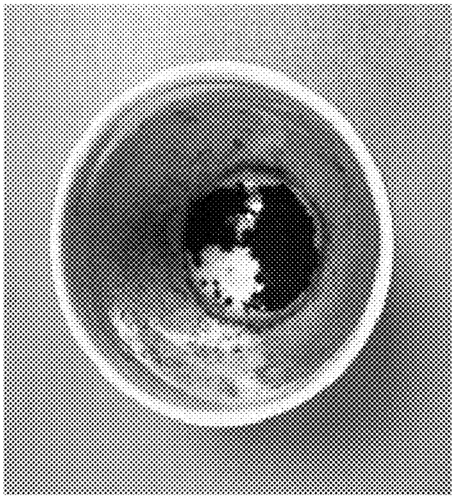
FIG. 3B illustrates GO powder obtained after filtering GO solution, according to an aspect of the present disclosure.
Figure 3C:
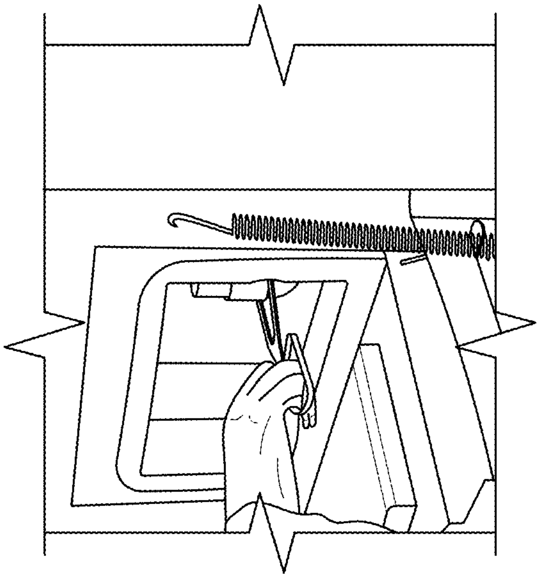
FIG. 3C illustrates a step of reduced graphene oxide (rGO) preparation, according to an aspect of the present disclosure.
Figure 3D:
FIG. 3D illustrates a 3D printed electrode, according to an aspect of the present disclosure.
Figure 3E:
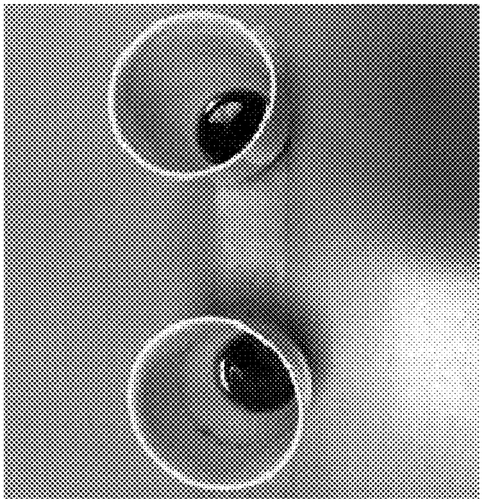
FIG. 3E illustrates a dip coating process, according to an aspect of the present disclosure.
Figure 3F:
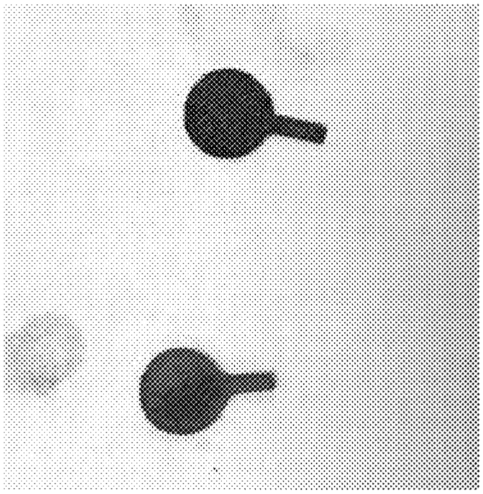
FIG. 3F illustrates rGO coated electrodes, according to an aspect of the present disclosure.

Filtering the GO is illustrated in FIG. 3A. The GO was washed with 300 ml of NaOH (2M), rinsed several times with DI water, and was left overnight to dry. The preparation of rGO is shown in FIG. 3B and FIG. 3C. The GO powder was added to three different crucibles that were left in a 400 °C muffle furnace for 1 min, 30 min, and 1 h, respectively. The electrode was 3D printed with a conductive PLA filament and was dip-coated in rGO+HCL and rGO+DMF solutions, as depicted in FIG. 3D and FIG. 3E. The electrodes were then left in the oven to dry at 100 °C for 15 min.

Figure 4:
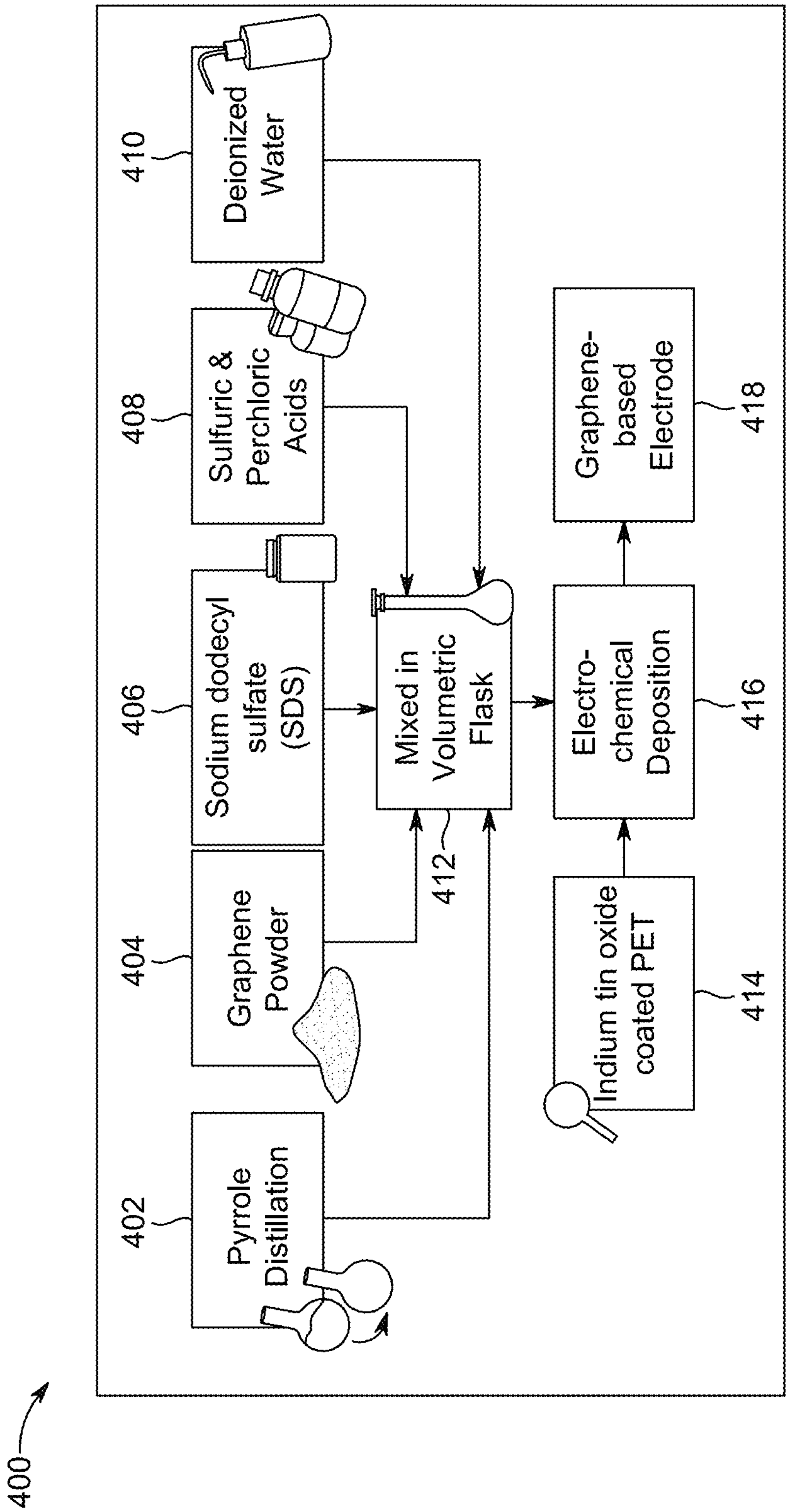
FIG. 4 illustrates a block diagram of manufacturing process of graphene electrode, according to an aspect of the present disclosure.

FIG. 4 illustrates a block diagram of the fabrication method 400 used to make the electrode. All the illustrated components were mixed to be used as a solution in an electrochemical deposition on PET. For example, pyrrole distillation 402, graphene powder 404, sodium dodecyl sulfate 406, sulphuric and perchloric acid 408 and deionized water 410 was mixed in a volumetric flask 412. Indium tin oxide coated PET 414 was added to the mixture 412 and the resultant was subjected to electrochemical deposition 416 to form the graphene-based electrode 418.

Figure 5A:
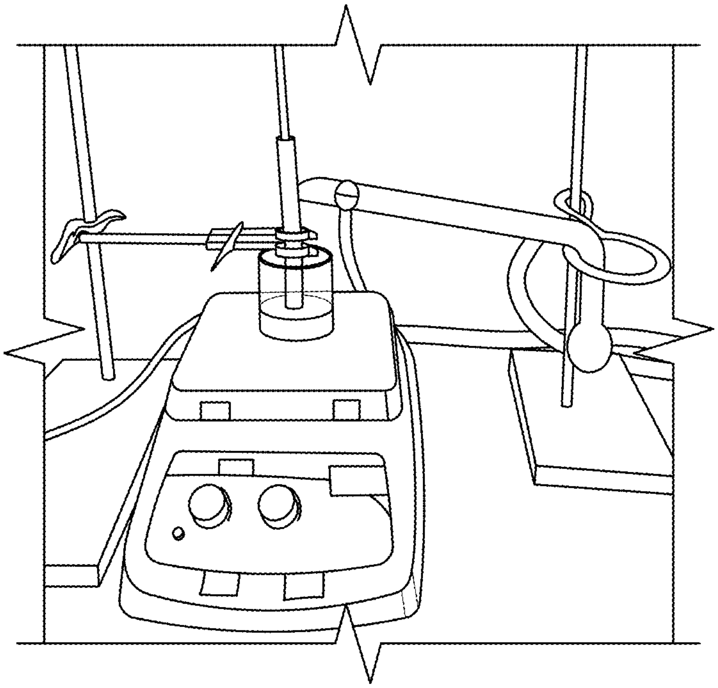
FIG. 5A illustrates a setup for pyrrole monomer purification process, according to an aspect of the present disclosure.
Figure 5B:
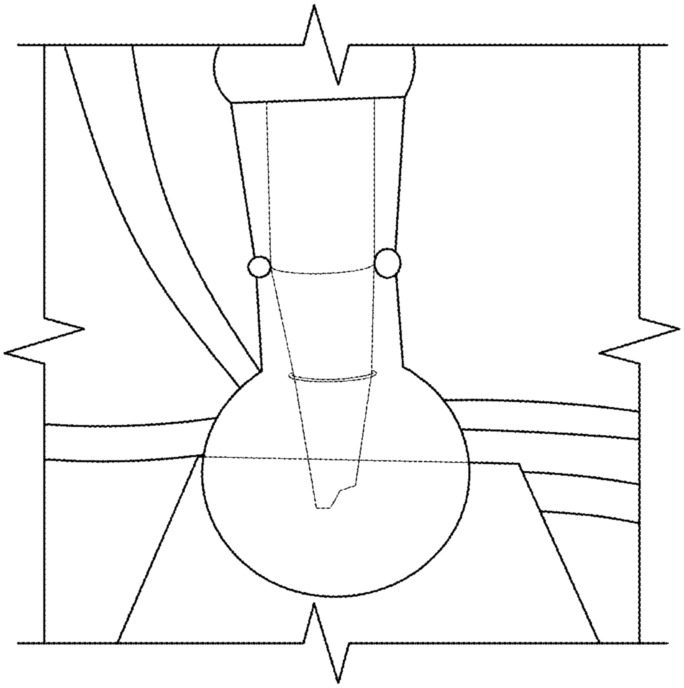
FIG. 5B illustrates purified pyrrole, according to an aspect of the present disclosure.

FIG. 5A depicts a process of pyrrole monomer purification. The sample was placed in an oil bath, and a distillation system was attached. Due to the heating, the sample evaporated, and vapors were allowed to pass through a condenser and then collect in the flask as shown in FIG. 5B.

To make the graphene-pyrrole sample, in a 50 ml volumetric flask, 440 mg of Sodium Dodecyl Sulphate (SDS) was mixed with DI water and 200 mg of graphene powder was added. Subsequently, 4 drops of sulfuric acid and 8 drops of perchloric acid were added. Lastly, 300 μl of purified pyrrole was added. Two samples were made using this method to test variation of scanning time in the electrochemical deposition.

Figure 6A:
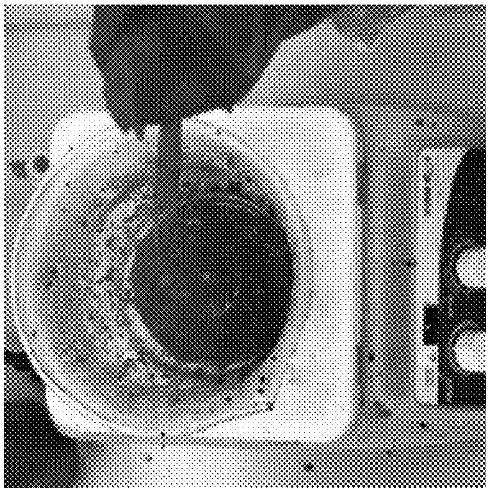
FIG. 6A illustrates GO solution, according to an aspect of the present disclosure.
Figure 6B:
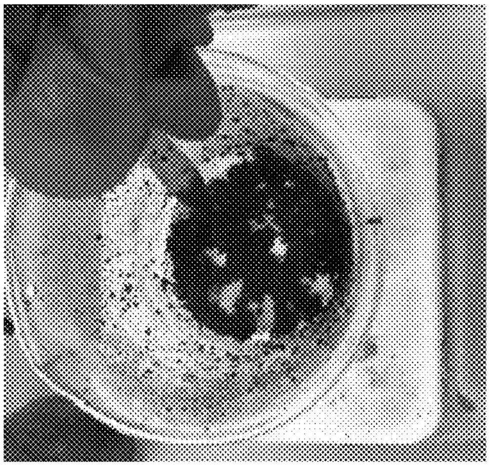
FIG. 6B illustrates wet GO, according to an aspect of the present disclosure.
Figure 6C:
FIG. 6C illustrates GO powder, according to an aspect of the present disclosure.
Figure 6D:
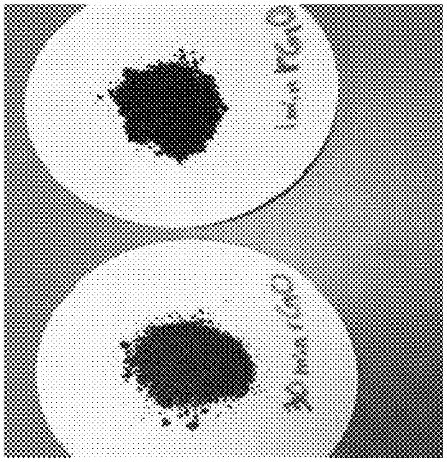
FIG. 6D illustrates rGO samples, according to an aspect of the present disclosure.

To prepare the rGO-pyrrole sample, two batches of GO were prepared (as described earlier), but by using graphene powder instead of the paste, and with a new washing process. 2150 ml of NaOH and 1200 ml of DI water were added to the GO solution to raise the pH, the mixture was left overnight in the oven at 90 °C. As shown in FIG. 6A, FIG. 6B, and FIG. 6C, the solution was heated at 100 °C and stirred until the GO was totally dry, to extract the GO powder. The rGO samples are shown in FIG. 6D, after the previously mentioned steps of forming the rGO were repeated. Two samples of rGO were prepared with the same steps of the graphene-pyrrole sample except that 3 g of rGO was added rather than the graphene.

The PET sheet was shaped as EEG electrodes (the wide end was cut after polymerization), as shown in FIG. 7A. The electrochemical cell was set with the reference electrode placed between the working electrode (holding the PET with the conductive side facing inwards) and the counter electrode (holding the graphite rod) and adding the composite solutions to obtain the electrodes as shown in FIG. 7B and FIG. 7C. Gamry Electrochemical Instrument was used for the polymerization process. The chronoamperometry technique was utilized with a voltage of 0.9V for 1 h for both the graphene-pyyrole and rGO-pyrrole solutions. As for the second sample of graphene-pyrrole, the same settings were used with the exception of being set for 1.5 h.

Example 2: Testing the Graphene-Based Electrode

Figure 9:
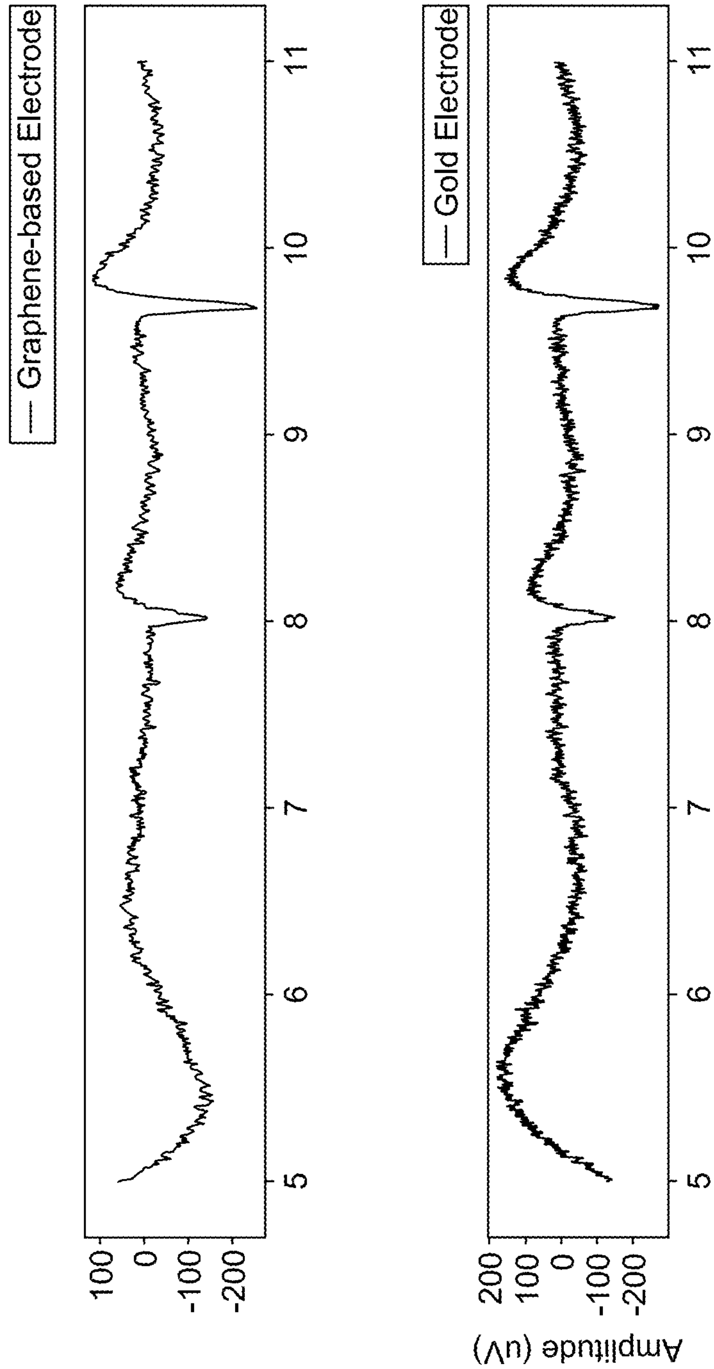
FIG. 9 illustrates filtered EMG signal of graphene-based electrode and conventional gold electrode, according to an aspect of the present disclosure.
Figure 10:
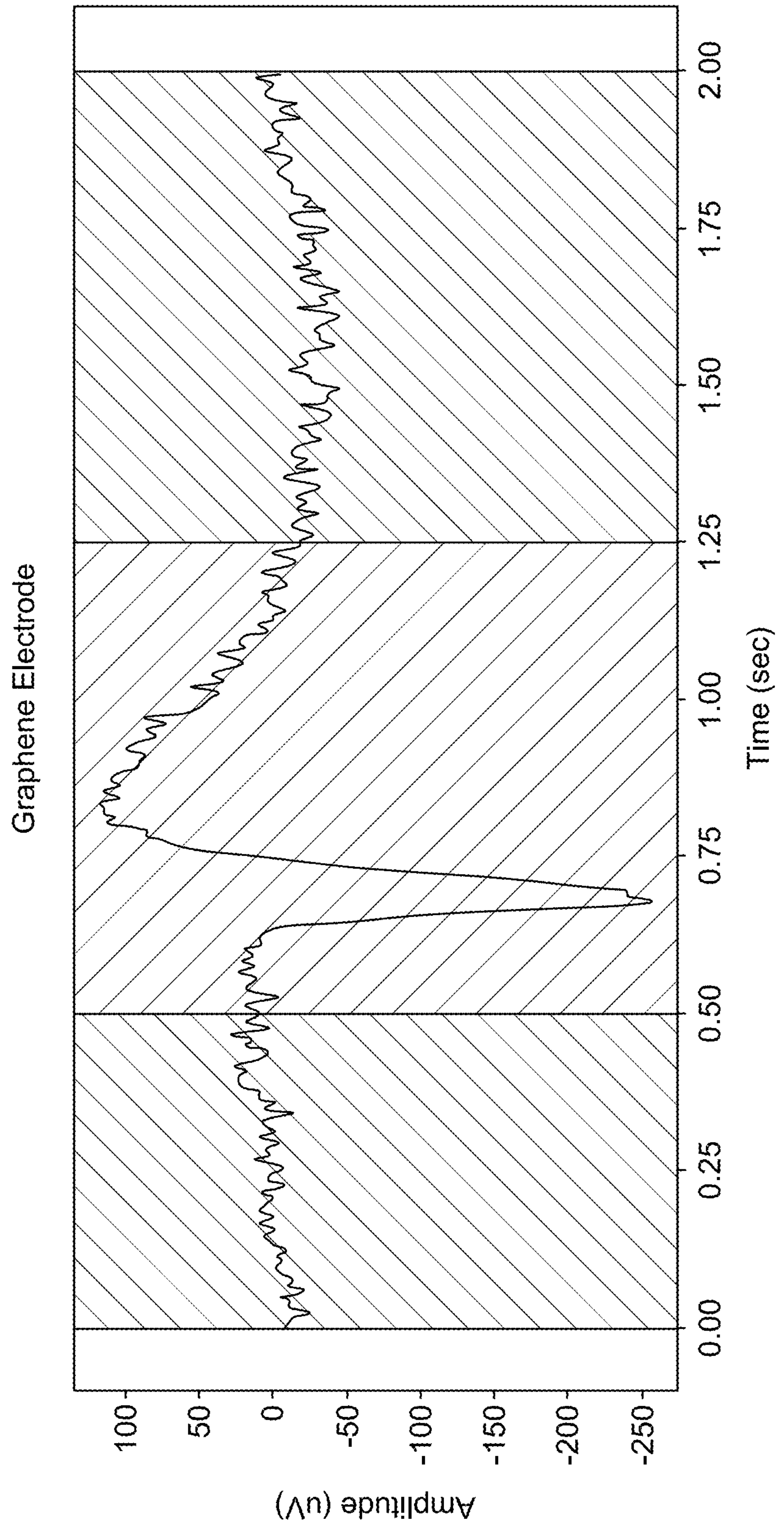
FIG. 10 illustrates a graphene-based electrode blink of 9 s to 11 s signal with a central portion indicating the signal and remaining portion indicating noise, according to an aspect of the present disclosure.

The electrode's functionality and efficacy were assessed by its ability to measure both brain activity (EEG) and muscle activity (EMG) using a standardized procedure described below familiar to those skilled in the art. Although embodiments of the present invention have been shown and described, it will be appreciated by those skilled in the art that changes, modifications, substitutions and alterations can be made in these embodiments without departing from the principles and spirit of the invention, the scope of which is defined in the claims and their equivalents. An EMG blinking experiment was conducted to verify the functionality of the electrode. One gold electrode was attached to channel Fp1 of the subject's forehead while also attaching the graphene electrode on channel Fp2 to simultaneously observe the output EMG signal. After obtaining the readings of the graphene-based electrode and gold electrode, the raw signal was processed. A notch filter was applied to remove the power line 60 Hz noise, while a bandpass filter of 0.5-50 Hz was used to reduce noise. The three post-filtering channels are shown in FIG. 9. To verify that the graphene-based electrode has higher SNR, a timeslot of 9 s to 11 s that illustrates a blink was chosen as the verification test. The 9 s to 11 s signal was partitioned into two sections, the signal, and noise as shown in FIG. 10. By measuring the power of the two signals, the SNR was measured. The blink SNR was measured using an equation (see Eq. 4) for each type of electrode. The signal was taken from the start of the blink (at 0.5s) to the end of the signal (at 1.25s). The remainder of the 2 s window was considered as the noise.

To plot and process EMG blinking verification test (on Python), the following exemplary code was used:

```
    import pandas as pd
    import matplotlib.pyplot as plt
    import numpy as np
    from scipy import signal
    from scipy.signal import freqz
    from scipy.signal import lfilter, butter
# Reading the data
    data = pd.read__csv('OpenBCIReadings.csv') # Has only 3 columns
    corresponding to 3 channels
    df = np.array(data) # converting the data to array
    t= np.arange(0, len(df))/250 # time
# plot signal from 9-11 sec
    plt.figure(figsize=(15,3))
    plt.plot(t[2250:2750], df[2250:2750,0])
    plt.xlabel(' Time (sec)')
    plt.ylabel(' Amplitude (uV)')
    plt.title(' Unfiltered signal (from 9-11 sec)')
# The data is noisy, which means we need to use filters
# 1) Notch filter to remove 60 Hz noise (power-line noise)
fs = 250.0 # Sample frequency (Hz)
f0 = 60.0 # Frequency to be removed from signal (Hz)
Q = 20.0 # Quality factor
# Design notch filter
    b, a = signal.iirnotch(f0, Q, fs)
    filtered__60Hz =[ ]
    for i in range(3):
      filtered__60Hz.append(signal.filtfilt(b, a, df[:,i]))
filtered__60Hz = np.array(filtered__60Hz).T
plt.plot(t[1250:2750], filtered__60Hz[1250:2750,0])
plt.xlabel(' Time (sec)')
plt.ylabel(' Amplitude (uV)')
plt.title(' Filtered Signal (60 Hz) (2sec duration)')
# 2) Bandpass filter (0.5-20 Hz)
    def butter__bandpass(lowcut, highcut, fs, order=5):
    nyq = 0.5 * fs
    low = lowcut / nyq
    high = highcut / nyq
    b, a = butter(order, [low, high], btype='band')
    return b, a
def butter__bandpass__filter(data, lowcut, highcut, fs, order=5):
    b, a = butter__bandpass(lowcut, highcut, fs, order=order)
    y = lfilter(b, a, data)
    return y
```

-continued

```
# desired cutoff frequencies (in Hz).
lowcut = 0.5
highcut = 50
m, s = butter_bandpass(lowcut, highcut, fs, order=4)
bandpassed_signal = [ ]
for j in range(3):
bandpassed_signal.append(butter_bandpass_filter(filtered_60Hz[:,j],
lowcut, highcut, fs, order=4))
bandpassed_signal = np.array(bandpassed_signal).T
plt.figure(figsize=(16, 8))
plt.subplot(3, 1, 1)
plt.plot(t[2250:2750], bandpassed_signal[2250:2750,0],
label='Graphene-based Electrode')
plt.legend( )
plt.subplot(3, 1, 2)
plt.plot(t[2250:2750], bandpassed_signal[2250:2750,1], label='Gold
Electrode')
plt.legend( )
plt.ylabel(' Amplitude (uV)')
plt.subplot(3, 1, 3)
plt.plot(t[2250:2750], bandpassed_signal[2250:2750,2],
label='Pyyrole Electrode')
plt.legend( )
plt.xlabel('Time (sec)')
```

Figure 11:
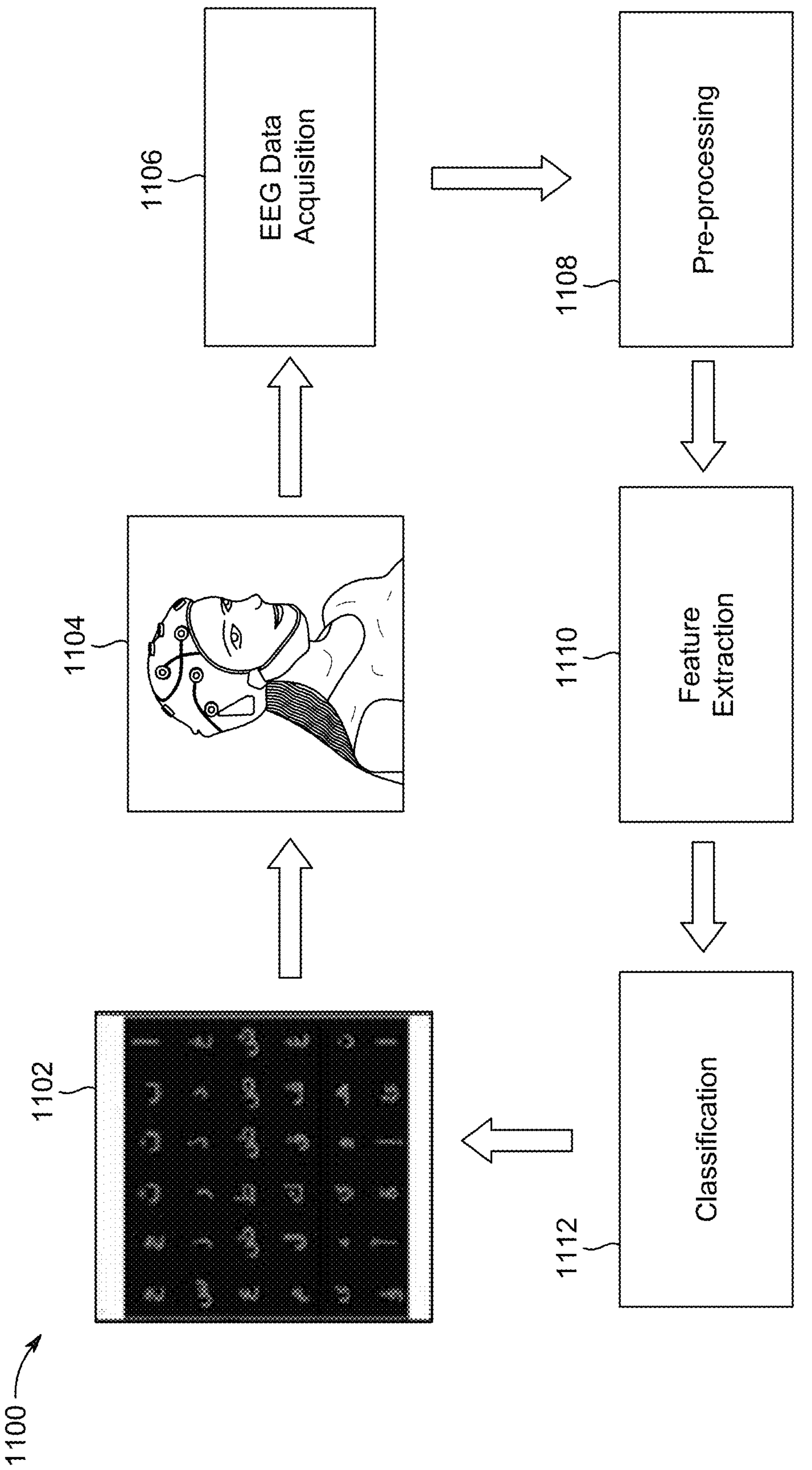
FIG. 11 illustrates a block diagram of P300 based Arabic speller, according to an aspect of the present disclosure.

FIG. 11 illustrates a schematic block diagram 1100 of the P300-based Arabic speller. First, the speller was displayed on a screen 1102 in front of the subjects 1104. Then, at block 1106, the EEG data was acquired by the Open ViBE software using the EEG cap. Subsequently, the data was pre-processed at block 1108, and the features were extracted (at block 1110) to classify the target and non-target waveforms (at block 1112). This process was repeated for all subjects. 15 subjects participated in the experiment (7 males and 8 females). None of the subjects suffered from any physical or mental health issues. The participants gave their consent and had no prior experience of P300 speller when conducting the experiment. To sample brain activity (EEG), an OpenBCI Cyton Biosensing Board was used, and it was connected to a PC through a dongle, as shown in FIG. 12A. The OpenBCI Cyton Biosensing Board contained 8-channel neural interface with a 32-bit processor. At each channel, data were sampled at 250 Hz. An EEG Electrode Cap Kit from OpenBCI, using the internationally recognized 10-20 electrodes placement system, shown in FIG. 12B, was used to record the EEG signal. OpenBCI GUI v5.0.8 was used to acquire and process data. OpenViBE Designer v3.1.0 was used to create scenarios for data acquisition and feature extraction. A Cyton board was connected via OpenViBE Acquisition Server where the driver was chosen as OpenBCI with modified index names of the electrodes' channels.

Figure 13A:
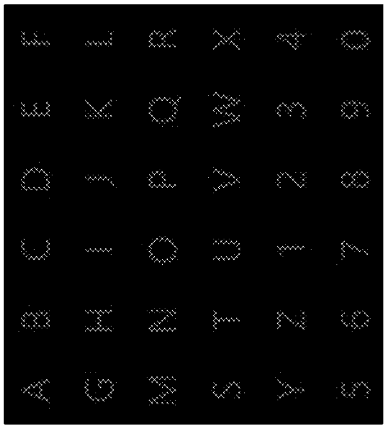
FIG. 13A illustrates an original display of the P300-based English speller, according to an aspect of the present disclosure.
Figure 13B:
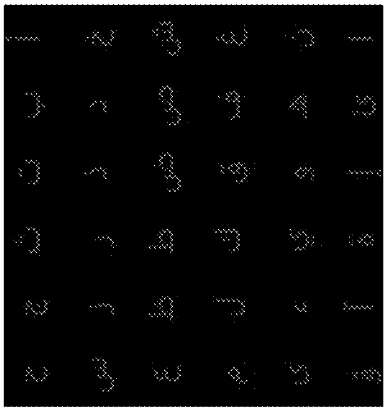
FIG. 13B illustrates a display of the P300-based Arabic speller, according to an aspect of the present disclosure.
Figure 14:
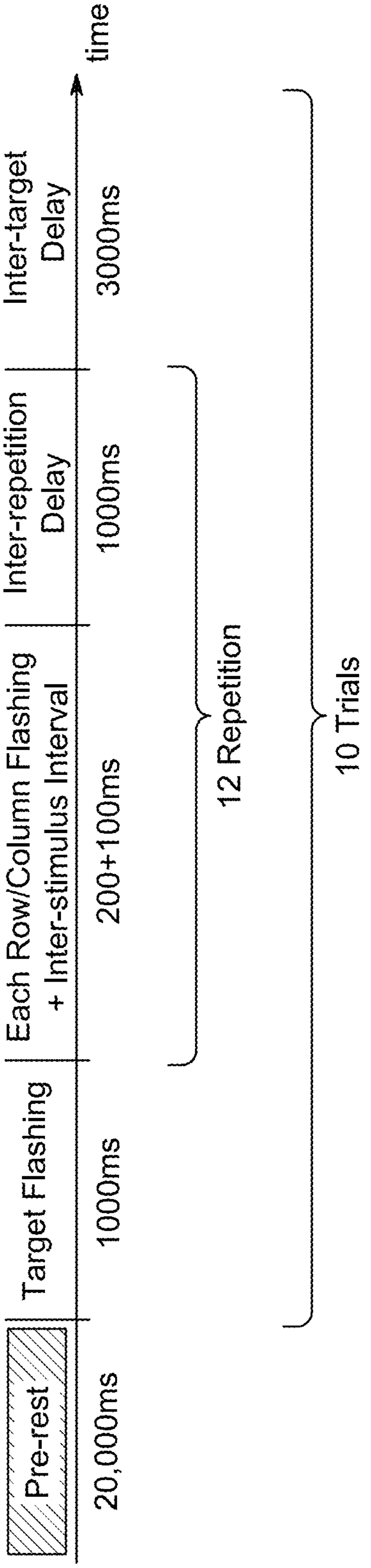
FIG. 14 is a block diagram of an experimental paradigm, according to an aspect of the present disclosure.

The subjects were seated 0.6 m from a 27-inch screen while instructed to not move or blink unnecessarily. The original speller visualizer had a 6×6 matrix containing English characters (see FIG. 13A) that was then converted to Arabic letters as shown FIG. 13B. The background of the speller was set to black, while the letters were grey until they flashed in white. All subjects completed the experiment using the Arabic speller. FIG. 14 illustrates a simplified experimental paradigm of the procedure. The session started with 20 s as a pre-rest. Then, the first target character was flashed in blue with a duration of 1000 ms for the subject to focus on. For each participant, 10 trials were completed. Every trial had 12 repetitions that flashed each row and column. A single repetition had an inter-repetition-delay of 1 s, allowing the user to rest. The flashes were intensified for 200 ms with an inter-stimulus-interval (ISI) of 100 ms. A rest duration of 3 s between each target character was employed. To further evoke the P300 signal, the participants were asked to count the number of times the desired character flashed. Each target character had a total of 24 flashes.

Figure 15:
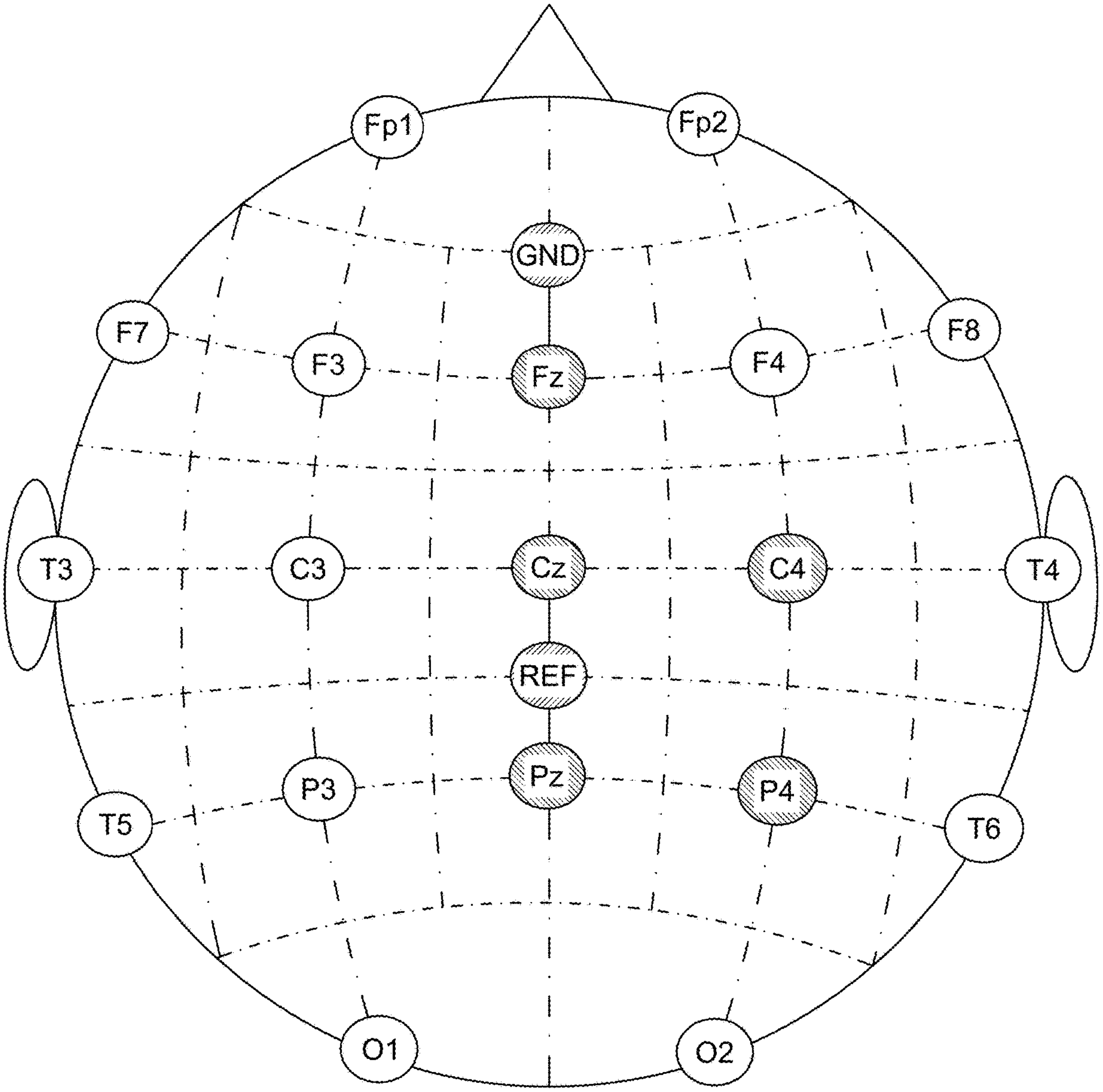
FIG. 15 illustrates placement of the EEG electrodes, according to an aspect of the present disclosure.

To acquire the EEG signal, Ag/AgCI EEG electrodes were placed on the parietal, centre, and frontal regions via (Pz, P4, Cz, C4, Fz) channels. A ground electrode and a reference electrode were also placed. The EEG electrodes placement is illustrated in FIG. 15. The impedance of the electrodes for all subjects was kept under 10 kΩ. OpenBCI had a band-pass filter of 5-50 Hz, and a band-reject filter that eliminates the noise at 60 Hz in Saudi Arabian powerlines. The obtained EEG signals were stored in .OV [dot OV] format and filtered by a 4th-order Butterworth band-pass filter to reject any signals outside the band 1-20 Hz. A pass-band ripple of 0.5 dB was set to account for the variation in the amplitude within the designated filter.

The most distinguishing qualities of a data set were the features. When a subject spotted a desired character, the generated signal was the target. In contrast, when any other row and column that does not contain the desired letter was flashed, the obtained waveform was the non-target. To distinguish the two cases, features were necessary. Mean and standard deviation were used to train the classifier. The EEG epochs were acquired using OpenViBE. Using an LDA classifier, the data was split into training and testing sets. The accuracy was then computed by Open ViBE.

To plot the P300 wave from the average target and non-target epochs (on MATLAB), the following code was used:

```
%Ch1 = C4
%CH2 = P4
%CH3 = Pz
%CH4 = Cz
%CH5 = Fz
close all;
clear all;
clc;
T = csvread('Target.CSV');
nT = csvread('NonTarget.CSV');
%% No smoothing
t=[0:((length(T)/250)/199): (length(T)/250)];
figure (1)
plot(t,T(:,3),'Line Width',2.0)
hold on
plot(t,nT(:,3),'--','Line Width',2.0)
legend('Target','Non Target');
title('Subject # Channel ( )')
xlabel(' Time (sec)')
ylabel(' Amplitude (uV)')
%% Smoothing
t =[0:((length(T)/250)/199): (length(T)/250)];
t = smooth(t);
figure (2)
plot(t,smooth(T(:,3)),'Line Width',2.0)
hold on
plot(t,smooth(nT(:,3)),'--','Line Width',2.0)
legend('Target','Non Target');
title('Subject # Channel ( )')
xlabel(' Time (sec)')
ylabel(' Amplitude (uV)')
```

To train the classifier of the P300 speller, the mean and standard deviation of the epochs were found.

The mean, $\bar{x}$, was calculated with the formula:

$$\bar{x} = \frac{\sum_{i}^{n} x_i}{n}. \qquad \text{(Eq. 1)}$$

The standard deviation σ was calculated with the following formula:

$$\sigma = \sqrt{\frac{\sum_{i}^{n}(x_i - x)^2}{n-1}}, \quad \text{(Eq. 2)}$$

where $x_i$ is the $i^{th}$ sample and n is the total number of samples.

To find the p-value, the t-value was calculated by using this formula:

$$t = \frac{\bar{x}_1 - \bar{x}_2}{\sqrt{\left(s^2\left(\frac{1}{n_1}+\frac{1}{n_2}\right)\right)}}. \quad \text{(Eq. 3)}$$

To verify the designed electrodes' efficiency, signal-to-noise ratio was calculated with the formula below:

$$SNR = \frac{E_{peak}}{E_{noise}} = \frac{\frac{1}{p}\sum_{i=1}^{p} x_i^2}{\frac{1}{n}\sum_{i=1}^{n} x_i^2}, \quad \text{(Eq. 4)}$$

where E is the energy, p and n are the number of points in P300 peak and noise, respectively, and $x_i$ the amplitude of the signal.

For GO synthesis, the second GO washing method extracted an impure GO powder. The amount of GO powder (x) used in the polymerization process was calculated as follows:

The total amount of graphene used was 1 g, the resultant GO powder weighted 51 g and 3 g of GO powder was used in the polymerization process, $$\text{hence, } x = \frac{3}{51} = 58.8 \text{ mg, existing in 3 g of GO powder.} \quad \text{(Eq. 5)}$$

The amount used in the polymerizations for each ml:

$$\frac{\text{Amount of GO used}}{\text{Size of volumetric flask}} = \frac{58.8 \text{ mg}}{5 \text{ mL}} = 1.2 \text{ mg/mL} \quad \text{(Eq. 6)}$$

Following are a list of standards considered during design and evaluation of the graphene-based electrode.

| Code | Description |
|---|---|
| IEEE P2014.6 | Interface |
| IEEE P2048.5 | Safety |
| ISO 22077-1: 2015 | Health informatics medical waveform format Published April 2015 |
| ANSI/CTA-2060 | Standard for Consumer EEG File Format (Attuned Container Format) |
| P2731 | Standard for a Unified Terminology for Brain-Computer Interfaces |
| IEC 60601-2-26 | Medical electrical equipment Part 2-26: Particular requirements for the basic safety and essential performance of electroencephalographs |
| ISO/TR 19733: 2019(en)- | Nanotechnologies- Matrix of properties and measurement techniques for graphene and related two-dimensional (2D) materials |
| IEEE 21451-001-2017 | IEEE Recommended Practice for Signal Treatment Applied to Smart Transducers |
| IEC 62304: 2006 + AMD1: 2015 | Software |
| IEC 60601-1-10: 2007 + AMD1: 2013 | Closed-loop control |

Example 3: Design Considerations

The graphene-based EEG electrode acquired better signal, lead to an improved diagnostic procedure and more accurate diagnosis for the clinicians. Researchers at graphene Flagship examined the potential impact of graphene-based materials (GBMsgb) on human health [See: B. Fadeel et al., "Safety Assessment of Graphene-Based Materials: Focus on Human Health and the Environment", ACS Nano, vol. 12, no. 11, pp. 10582-10620, 2018, which is incorporated herein by reference in its entirety]. Graphene is safe and does not cause skin irritation after acute exposure. Hence, the proposed designed electrodes eliminate potential skin irritations and improves the health and welfare of an individual.

Graphene-based materials are a new and fast-growing segment owing to their tensile strength, mechanical properties, flexibility, and chemical stability. The proposed design can extend its application to global markets by utilizing it in different applications in various industries, such as electronics, biomedical, automotive, and construction.

Since the electrodes are graphene-based, they have an impact on the environment. To be environmentally friendly, materials need to be biodegradable, as the accumulation of foreign materials can damage the environment and cause health problems. The University of Strasbourg studied graphene itself and determined that it is biodegradable and safe for the environment [See: "Graphene Technologies Creating Environmentally Sustainable Solutions", INN, 2022, which is incorporated herein by reference in its entirety]. Graphene, owing to its properties, has the potential to replace more hazardous materials in various applications, leading to a reduction in environmental pollution. By replacing traditional materials with graphene-based alternatives, it is possible to reduce $CO_2$ emissions and aid in the production of biodegradable polymers [See: G. Costa and C. Hussain, "Ethical, legal, social and economic issues of graphene", Analytical Applications of Graphene for Comprehensive Analytical Chemistry, pp. 263-279, 2020, which is incorporated herein by reference in its entirety].

With the application of graphene in composite materials, where it is incorporated into a host polymeric material, its properties may be modified and improved. This made it possible to obtain a material that is much more flexible with the advantage of being able to introduce great electrical conductivity. The composite may enable the detection of diseases with greater accuracy in the medical field, which will, in turn, create a new strand of medical applications based on graphene. Therefore, the graphene-based electrode may impact the graphene production chain, resulting in immense economic benefits.

Following are a list of components used in the manufacture of the graphene-based electrode.

| Electrode | Materials |
|---|---|
| rGo coated 3D printed electrodes | Graphene Powder<br>Sulfuric Acid<br>Nitric Acid<br>NaOH<br>Ethanol<br>Dimethylformamide (DMF)<br>PLA Filament |
| rGo-Pyrrole composite electrode | Graphene Powder<br>Sulfuric Acid<br>Nitric Acid<br>NaOH<br>Indium tin oxide coated polyethylene terephthalate (PET) film<br>Pyrrole Polymer<br>Perchloric Acid<br>Sodium Dodecyl Sulphate SDS |
| Graphene-based electrode | Graphene Powder<br>Sulfuric Acid<br>Indium tin oxide coated polyethylene terephthalate (PET) film<br>Pyrrole Polymer<br>Perchloric Acid<br>Sodium Dodecyl Sulphate SDS |

Following table depicts a cost analysis of rGO coated 3D printed electrodes.

| Material | Bulk Volume/Size | Bulk Price (SAR) | Volume/Size Used | Net Price (SAR) |
|---|---|---|---|---|
| Graphene Powder | 10 g | 700 | 0.05 g | 3.5 |
| Sulfuric Acid | 2.5 L | 535 | 60 ml | 12.84 |
| Nitric Acid | 2.5 L | 1205 | 20 ml | 9.64 |
| NaOH | 1 kg | 197 | 20 g | 3.94 |
| Ethanol | 500 ml | 499.3 | 2 ml | 1.99 |
| Dimethylformamide (DMF) | 2.5 L | 1149.18 | 2 ml | 9.2 |
| 3D printed PLA filament | Printed as per design | | | 50 |
| Net Price for one Electrode | | 91.11 | | |

Following table depicts a cost analysis of rGO-pyrrole deposited electrodes.

| Material | Bulk Volume/Size | Bulk Price (SAR) | Volume/Size Used | Net Price (SAR) |
|---|---|---|---|---|
| Graphene Powder | 10 g | 700 | 0.05 g | 3.5 |
| Sulfuric Acid | 2.5 L | 535 | 60 ml | 12.84 |
| Nitric Acid | 2.5 L | 1205 | 20 ml | 9.64 |
| NaOH | 1 kg | 197 | 20 g | 3.94 |

-continued

| Material | Bulk Volume/Size | Bulk Price (SAR) | Volume/Size Used | Net Price (SAR) |
|---|---|---|---|---|
| Indium tin oxide coated polyethylene terephthalate (PET) film | 1 sheet ($16.5\ cm^3$) | 158.11 | $0.039\ cm^3$ | 0.37 |
| Pyrrole Polymer | 25 ml | 118.25 | 0.3 ml | 1.42 |
| Perchloric Acid | 100 ml | 134 | 4 drops (0.2ml) | 0.268 |
| Sodium Dodecyl Sulphate SDS | 25 g | 300.75 | 0.44 | 5.29 |

Following table depicts a cost analysis of graphene-pyrrole deposited electrodes.

| Material | Bulk Volume/Size | Bulk Price (SAR) | Volume/Size Used | Net Price (SAR) |
|---|---|---|---|---|
| Graphene Powder | 10 g | 700 | 0.2 g | 14 |
| Sulfuric Acid | 2.5 L | 535 | 8 drops (0.4 ml) | 0.0856 |
| Indium tin oxide coated polyethylene terephthalate (PET) film | 1 sheet ($16.5\ cm^3$) | 158.11 | $0.039\ cm^3$ | 0.37 |
| Pyrrole Polymer | 25 ml | 118.25 | 0.3 ml | 1.42 |
| Perchloric Acid | 100 ml | 134 | 4 drops (0.2 ml) | 0.268 |
| Sodium Dodecyl Sulphate SDS | 25 g | 300.75 | 0.44 | 5.29 |
| Net Price (SAR) | | 21.4336 | | |

Based on the above cost analysis, the designed graphene-pyrrole electrode was considered cost effective compared to the commercially available products. The final electrode design was drawn using SOLIDWORKS software (see FIGS. 23A to D). Solidworks is a product by SolidWorks Corp, Dassault Systèmes, Massachusetts, USA. The electrode is designed to have a thickness of 0.5 mm, radius of 5.0 mm and a tail with length of 6.0 mm and width of 2.0 mm.

Example 4: Experimental Verification

Figure 16:
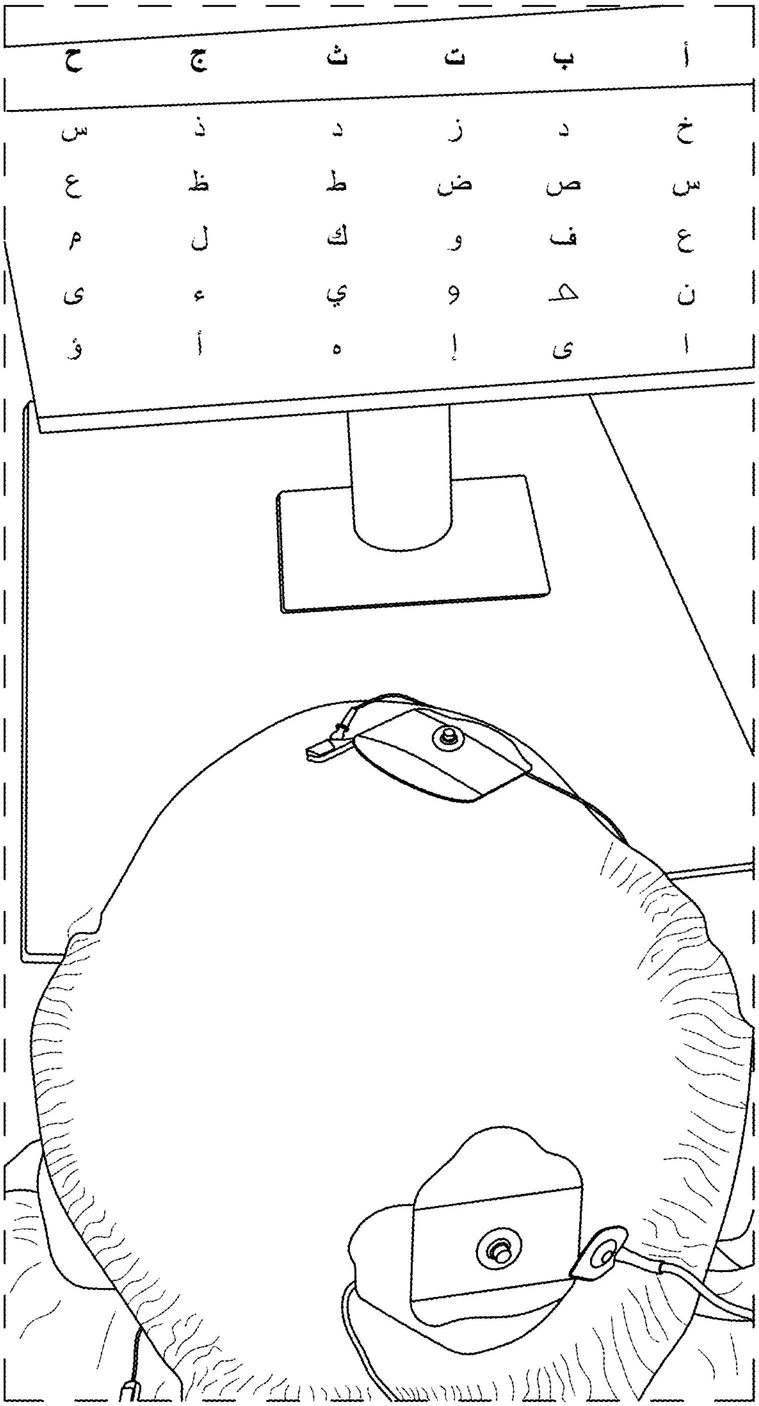
FIG. 16 illustrates placement of graphene-based electrode and the conventional gold electrode on channels P4 and Fz, according to an aspect of the present disclosure.

P300 experiment was conducted to verify the manufacturing of a dry graphene-based electrode to increase SNR compared to the conventional electrodes and employing the dry graphene-based electrode on a P300-based Arabic speller. The experiment was conducted by attaching two graphene-based electrodes and two conventional gold electrodes in Fz and P4 channels simultaneously, as shown in the FIG. 16. Subsequently, the signal was obtained, and SNR was computed.

Figure 17:
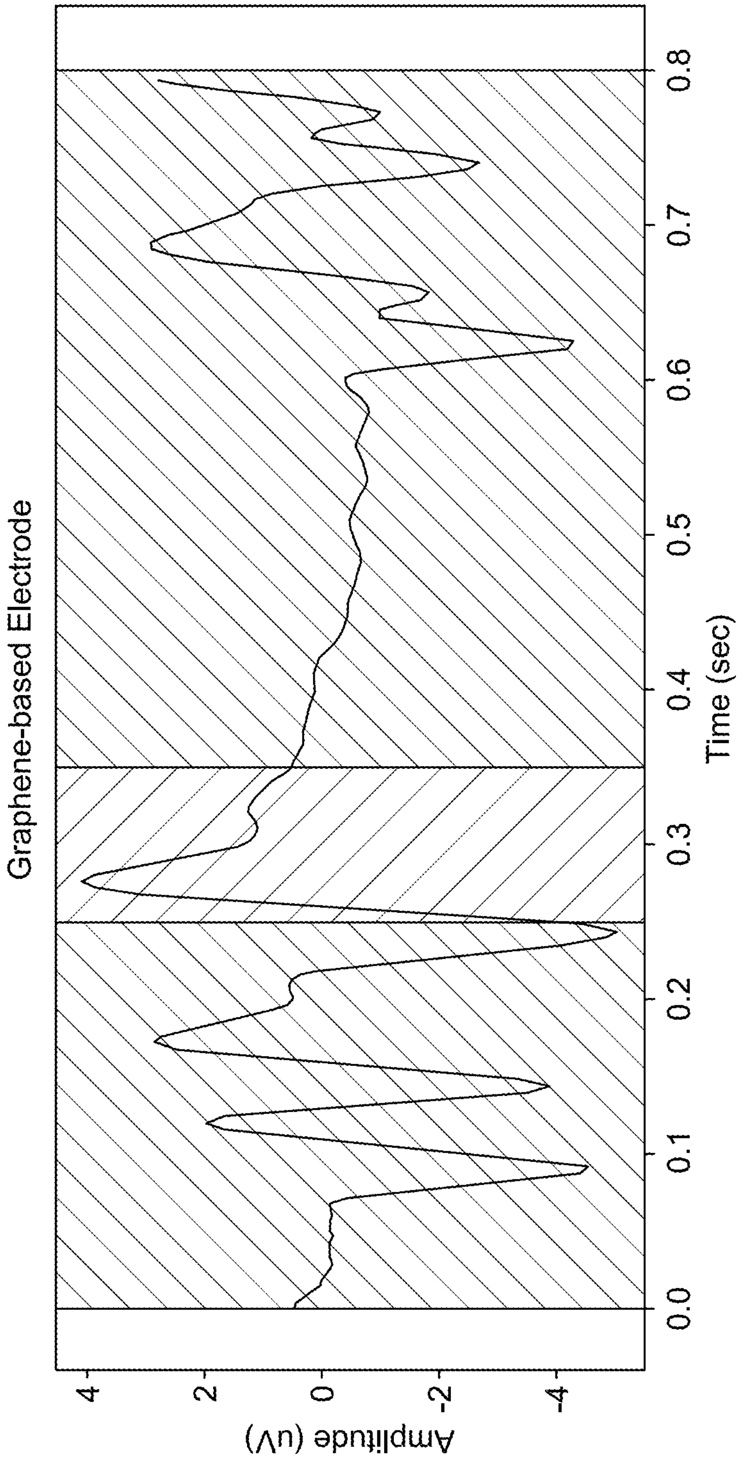
FIG. 17 illustrates the graphene-based electrode P300 target signal with a central hatch portion indicating the signal and other hatched regions indicating noise, according to an aspect of the present disclosure.

Further processing was performed after recording the P300 EEG data. An offline analysis, using the train classifier scenario, was performed in Open ViBE to obtain the accuracy of the experiment. The averaged epochs were derived from the scenario to analyse thereof and measure the SNR. After plotting a target signal, the amplitudes and latency of each channel and electrode were noted. To capture the P300 peak, a duration of 0.25 s to 0.30 s was chosen as a peak signal. The remainder signal was considered as noise. FIG. 17 illustrates form of the splitting.

Example 5: Results

After conducting the Arabic P300 speller experiment, the following results were obtained. From the table below, it will be noticed that the accuracy obtained from the graphene is slightly higher than the conventional gold electrode.

| Type of Electrode | Graphene-based | Gold |
|---|---|---|
| Accuracy | 87.680556% | 85.27778% |

Figure 18A:
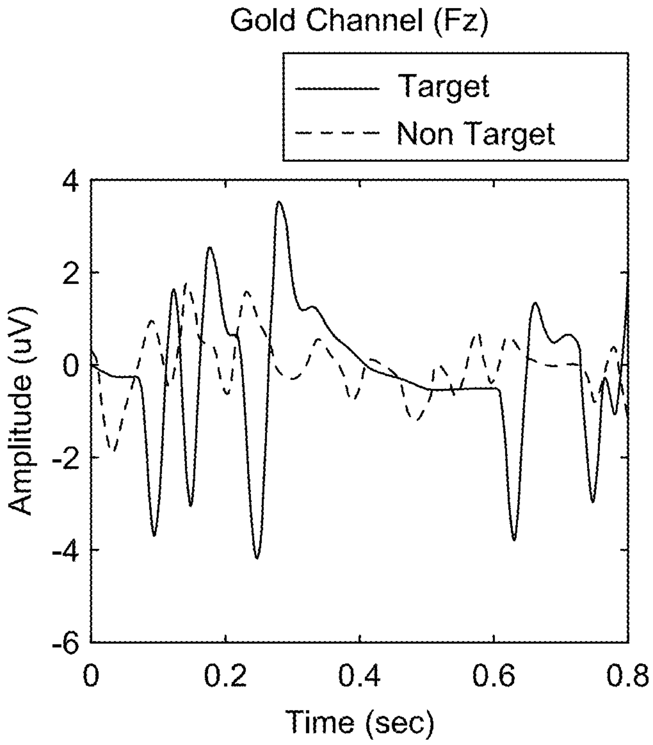
FIG. 18A illustrates a graph of target stimuli and non-target stimuli of Fz channel for conventional gold electrode, according to an aspect of the present disclosure.
Figure 18B:
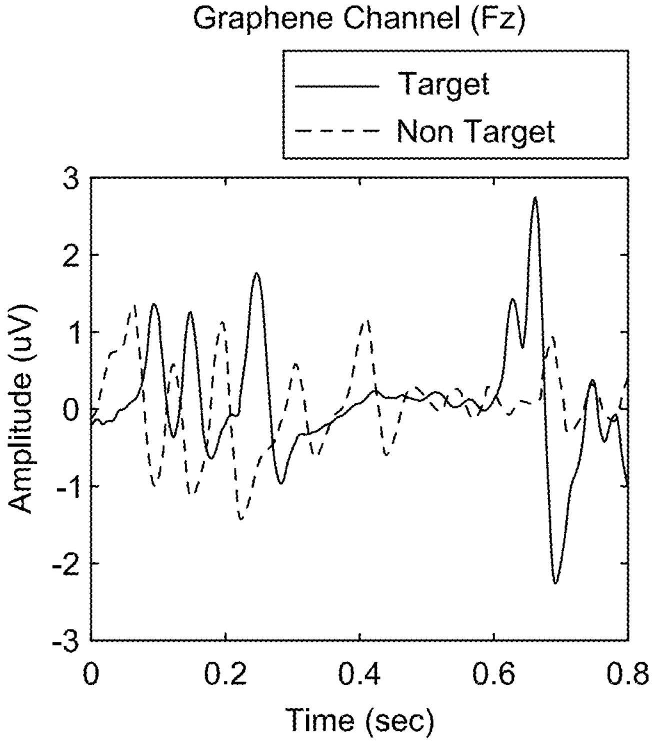
FIG. 18B illustrates a graph of target stimuli and non-target stimuli of Fz channel for graphene electrode, according to an aspect of the present disclosure.
Figure 18C:
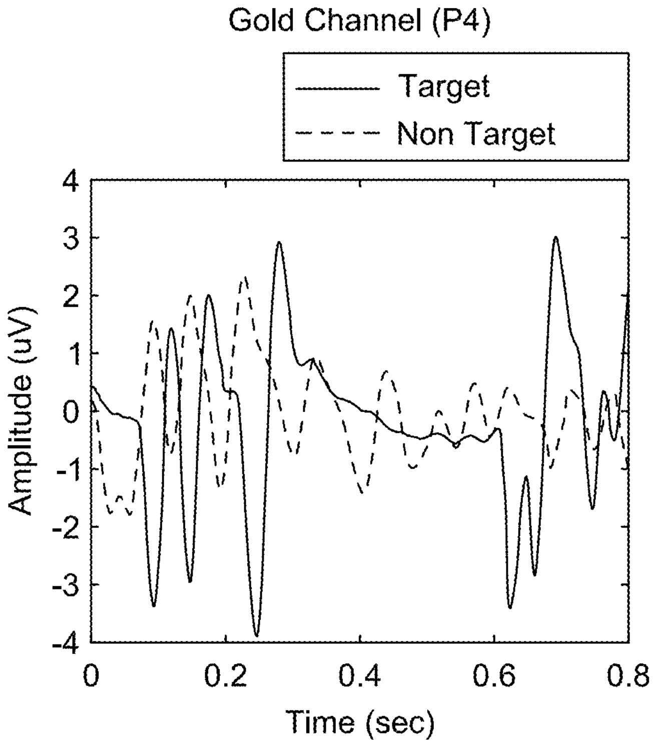
FIG. 18C illustrates a graph of target stimuli and non-target stimuli of P4 channel for conventional gold electrode, according to an aspect of the present disclosure.
Figure 18D:
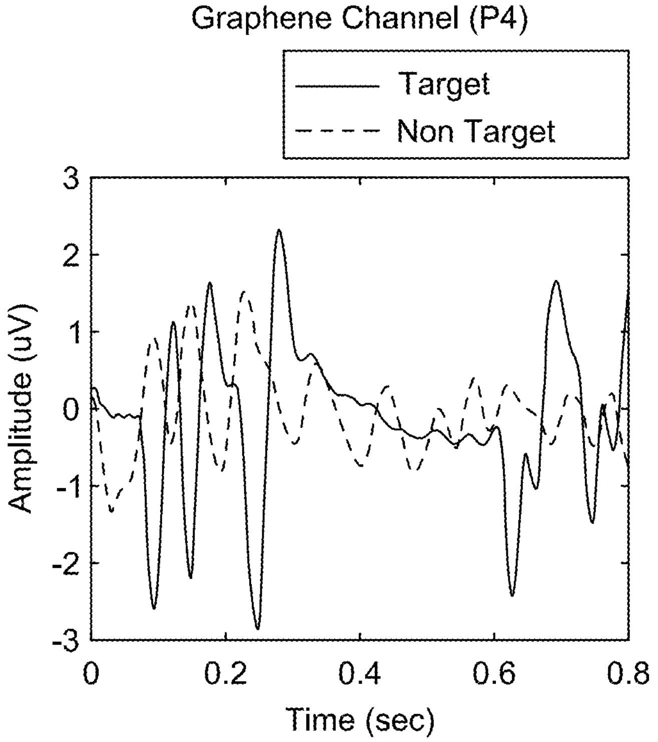
FIG. 18D illustrates a graph of target stimuli and non-target stimuli of P4 channel for graphene electrode, according to an aspect of the present disclosure.

As may be noticed from FIG. 18C and FIG. 18D, the channel Pz was identical in both electrodes while having a higher amplitude in the conventional. A downside of the gold electrode was the second peak seen around 750 ms, which might be interpreted as a stimulus. In channel Fz, however, the signal was quite different. A plausible reason was the placement. Since the two electrodes were next to each other on point Fz, one might have been out of range. Overall, the amplitudes and latency were sufficient. Due to the similarity of the two electrodes' signal, an SNR test was conducted on channel P4 to determine a better signal. The SNR was determined using Eq. 4. As indicated in table below, the SNR of the graphene-based electrode was higher than that of the conventional electrode.

| Type of Electrode | Graphene-based | Gold |
|---|---|---|
| SNR | 1.907 | 1.569 |

Figure 19A:
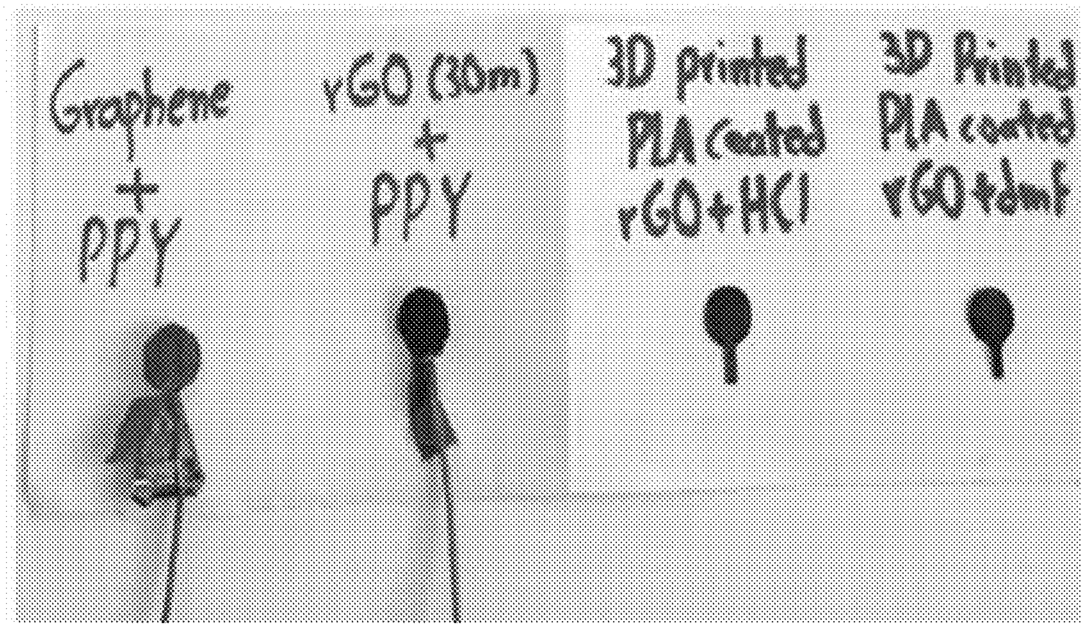
FIG. 19A illustrates resultant graphene-based electrodes, according to an aspect of the present disclosure.

FIG. 19A depicts the fabricated electrodes. The overall designs of all the electrodes were sufficient and flexible. With the aid of Fourier Transform Infrared Spectroscopy (FTIR), some of the functional groups were confirmed and helped to detect the functional groups existed in the compound materials.

Figure 19B:
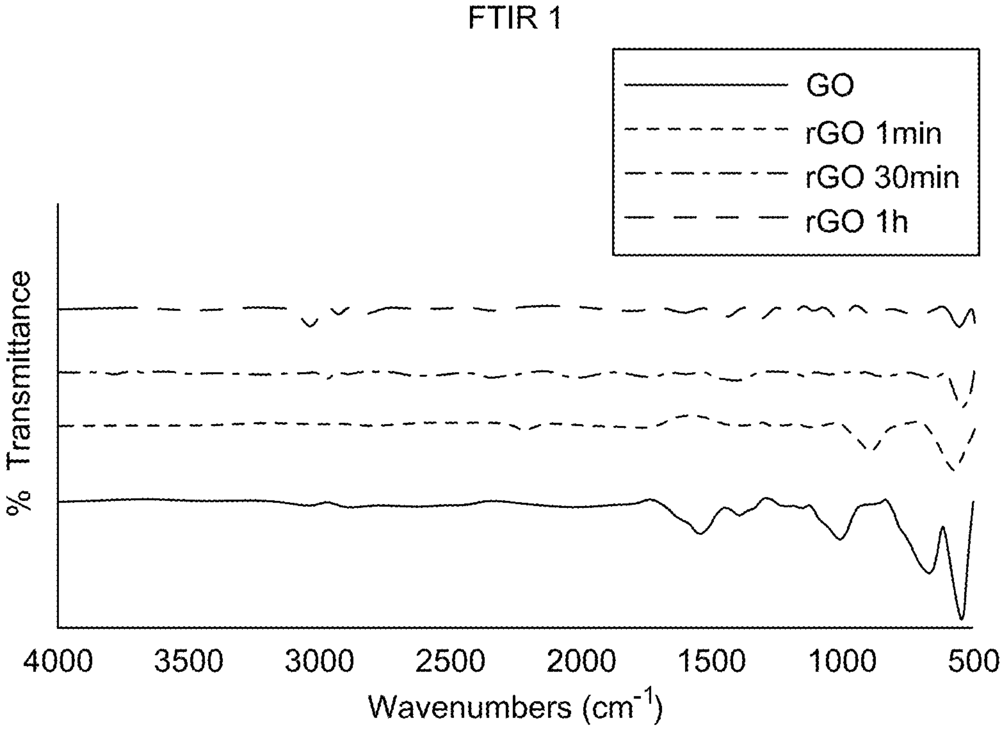
FIG. 19B illustrates Fourier transform infrared (FTIR) of first GO washing method, according to an aspect of the present disclosure.

FIG. 19B shows the FTIR of the first GO washing method and the resultant rGO samples. Looking at GO spectrum, OH stretching peak around 3000 $cm^{-1}$ does not exist. Since least amount of GO powder was extracted during the filtering process, most of it was fully dispersed in the solution, this indicates that the extracted powder may be excess graphene not GO.

Figure 19C:
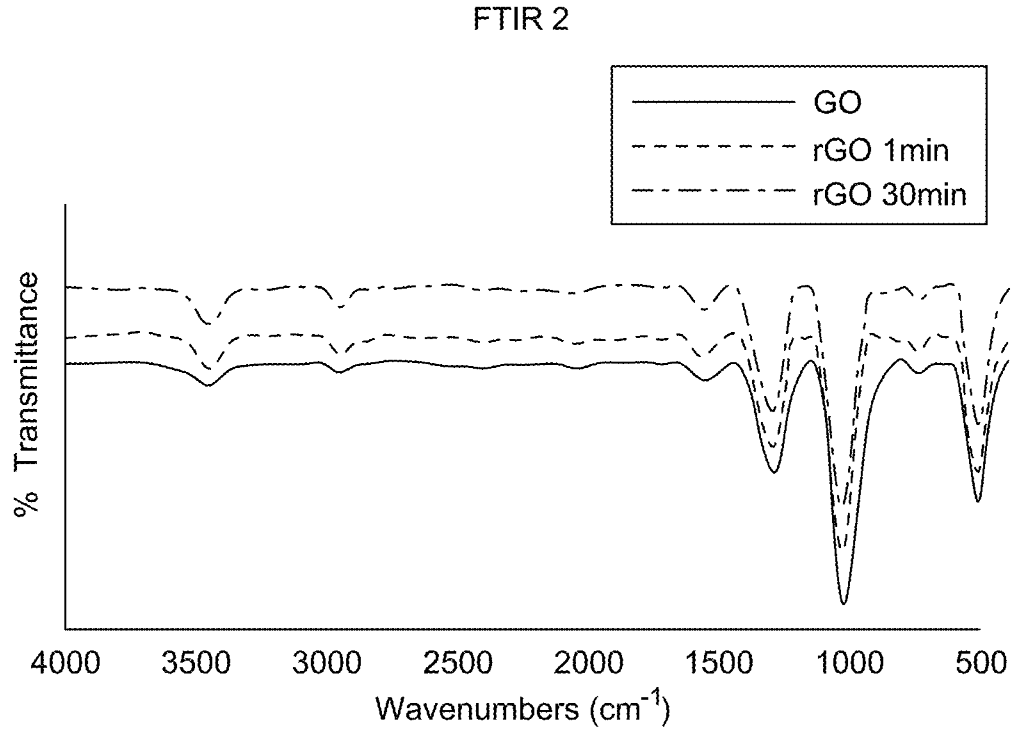
FIG. 19C illustrates FTIR of second GO washing method, according to an aspect of the present disclosure.

For the second GO washing method, filter process was removed to gain bigger quantity of GO and minimize the losses. However, when all the water evaporated, some crystals started to form, and the extracted GO powder's weight was greater than the starting weight. Thus, the resultant GO powder was impure. Therefore, the concentration of GO was calculated using Eq. 5 and Eq. 6. Referring to FIG. 19C, the FTIR of GO contains many peaks such a slight OH stretching, C—O stretching, and asymmetric COO stretching peaks which appeared around 3000 $cm^{-1}$, 1100 $cm^{-1}$ and 1425 $cm^{-1}$, respectively. These peaks were indicative of a high probability of presence of one of the chemicals already existed in the powder.

Figure 19D:
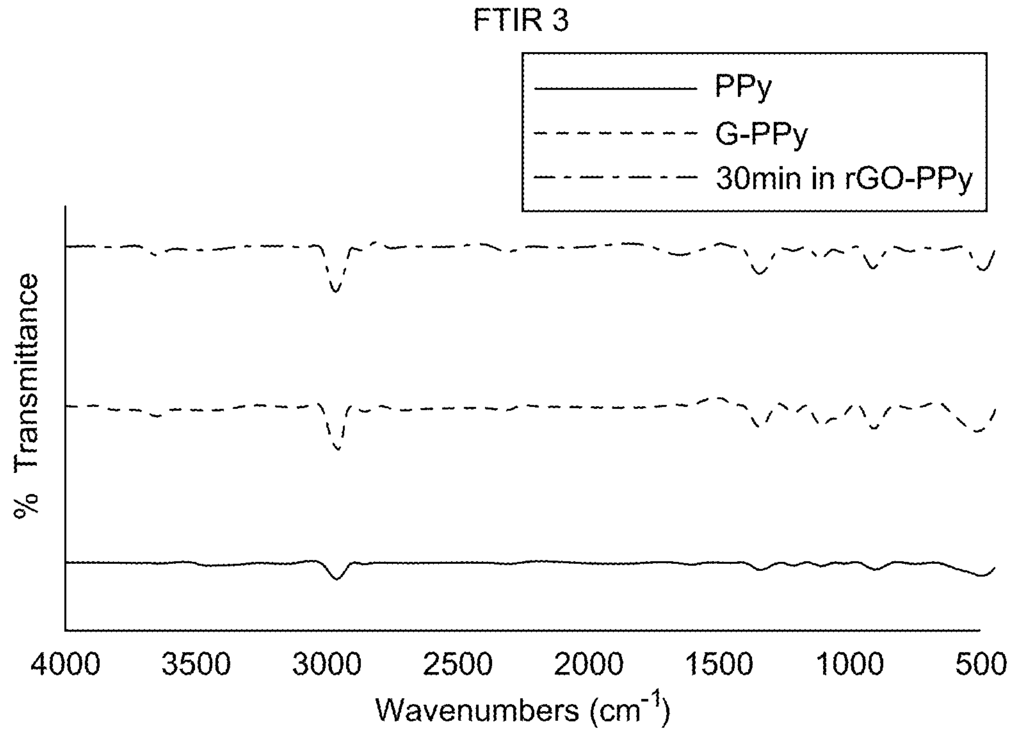
FIG. 19D illustrates FTIR after polymerization, according to an aspect of the present disclosure.

Referring to FIG. 19D, in the PPy spectrum, neither C—N stretch round 1025-1200 $cm^{-1}$ nor N—H stretch around 3500 $cm^{-1}$ were detected. However, a peak was observed at 3000 $cm^{-1}$ which could belong to other materials existed in the aqueous solution. Furthermore, in comparing PPy spectrum with graphene-PPy spectrum, the peak at 3000 $cm^{-1}$ increased. Since it was added to the PPy solution, it was indicated that the increase in peak was due to the graphene which in return gave evidence that graphene was deposited on the PET sheet. The SNR for the different type of electrodes were calculated as shown in table below.

| Type of Electrode | Graphene-based | Gold |
|---|---|---|
| SNR | 16.96 | 11.10 |

From the above table, it is apparent that the graphene-based electrode produces better signals based on the high SNR value of 16.96 compared to the 11.1 SNR value of the conventional gold electrode. This may be associated with the 2 dimensionality of the graphene [See: Rastegar, S., Stadlbauer, J., Pandhi, T., Karriem, L., Fujimoto, K., Kramer, K., Estrada, D. and Cantley, K., 2019. Measurement of Signal-to-Noise Ratio in Graphene-based Passive Microelectrode Arrays. Electroanalysis, 31 (6), pp.991-1001, which is incorporated herein by reference in its entirety].

Figure 20:
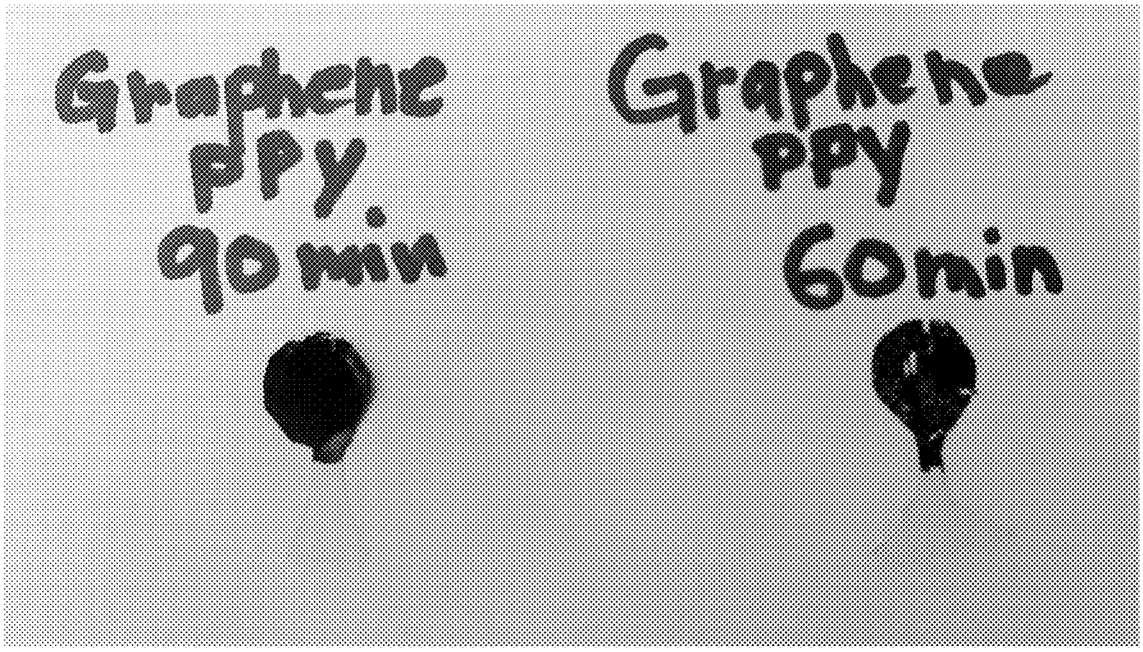
FIG. 20 illustrates two samples of the graphene-based electrodes with different electrochemical deposition time, according to an aspect of the present disclosure.

FIG. 20 depicts the graphene-based electrodes with different electrochemical deposition durations. After conducting the P300 experiment with these two electrodes, it was apparent that the 60 min deposited graphene-based electrode was not as sustainable as the 90 min electrode. It was inferred that with the increase in electrochemical deposition duration, amount of graphene-PPy deposition was more and a degree of disintegration was less.

After completing the experiment for the Arabic speller, and based on the results from 15 subjects, an accuracy above 85% was observed. Referring to the box plot in FIG. 21 and details provided in the table below, when the channels' amplitudes were compared for all subjects, it was observed that all channels provided adequate amplitudes for the P300. However, among all the channels, Pz channel provided the lowest amplitudes and mean for all subjects with 0.04 μV and 0.9157 μV, respectively. Even though Pz lies in the parietal region, which is one of the regions that detects ERP excellently, 4 out of 15 subjects recorded below 0.05 μV. This was due to the cap being very large for those four subjects and resulted in not attaching the electrodes to the scalp properly. Whereas, Fz channel obtained a highest mean, indicating that all subjects recorded high amplitudes. This may be explained by the association of the frontal lobes with more complex cognitive processes evoking ERP [See: O. Guy-Evans, "Frontal Lobe Function, Location in Brain, Damage, More|Simply Psychology", Simplypsychology.org, 2022, which is incorporated herein by reference in its entirety]. The P4 channel achieved the maximum amplitude between all channels with 4.3699 μV.

| Channels | Min | Max | Mean | SD |
|---|---|---|---|---|
| C4 | 0.9 | 3.6445 | 1.7649 | 1.017 |
| P4 | 1.05 | 4.3699 | 2.0949 | 1.2487 |
| Pz | 0.04 | 1.874 | 0.9157 | 0.6648 |
| Cz | 0.71 | 2.9338 | 1.4505 | 0.7983 |
| Fz | 1.87 | 3.664 | 2.4829 | 1.0503 |

A two tailed t-test was performed to test similarity of the amplitudes between the two channels (see table below). A cut-off for significance of 0.05 was used. The p-value less than 0.05 indicated a great difference between the means of two channels. For channels Fz and Cz, a significant difference between their means was indicated with $p=0.00002$. Four more groups had $p<0.05$, with these groups being: (P4 vs C4), (Fz vs C4), (Cz vs Pz), and (Fz vs Pz). Channels Fz and P4 slightly missed the significance level with $p=0.08912$. The highest p-value was for channels Cz and C4 with $p=0.9981$, indicating an insignificant difference, which is rational because these two channels lie in the same central region.

| Channels | C4 (n = 15) | P4 (n = 15) | Pz (n = 15) | Cz (n = 15) |
|---|---|---|---|---|
| P4 (n = 15) | p = 0.0348 | — | — | — |
| Pz (n = 15) | p = 0.9047 | p = 0.93388 | — | — |
| Cz (n = 15) | p = 0.9981 | p = 0.82785 | p = 0.00157 | — |
| Fz (n = 15) | p = 0.00013 | p = 0.08912 | p = 0.00003 | p = 0.00002 |

Figure 22:
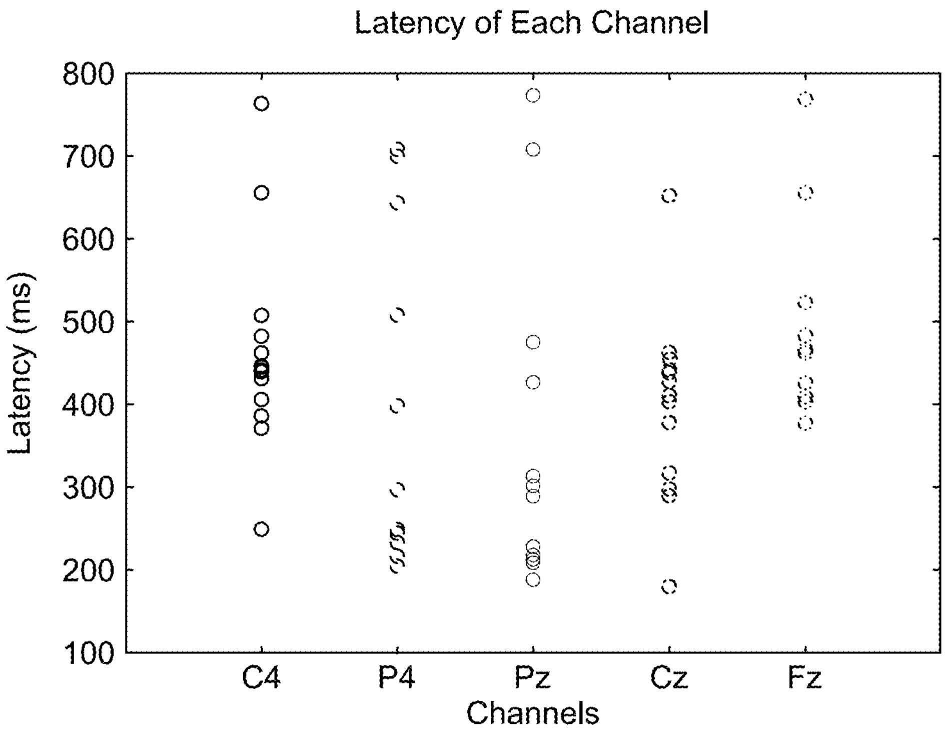
FIG. 22 is a scatter plot of the highest amplitude latency of each channel for all subjects, according to an aspect of the present disclosure.

From FIG. 22, it may be observed that a latency varied with different channels in a window of 800 ms. Latency is related to the difficulty in differentiating between the target stimuli and standard stimuli. The peak latency of simple discrimination in a subject typically varies between 200 ms to 800 ms [See: T. W. Picton, "The P300 Wave of the Human Event-Related Potential," Journal of Clinical Neurophysiology, which is incorporated herein by reference in its entirety]. Over the five channels, Fz had the longest latency with the shortest one being around 400 ms, as subjects with decreased cognitive abilities results in later P300 than normal [See: "The P300 Wave of the Human Event-Related Potential: Journal of Clinical Neurophysiology", LWW, which is incorporated herein by reference in its entirety]. The channel Pz provided the shortest latency between 200 ms to 320 ms, because of its critical position in the parietal region providing the fastest response to a target stimulus. Overall, most of the subjects provided acceptable range of latency for all channels to evoke P300.

To this end, it will be understood that electroencephalographic (EEG)-based brain-computer interfaces provide a linking medium between humans' brain and the computer. By using pure brain activity, users are able to control computers via brain-computer interfaces (BCIs). One of the problems that remain unsolved is the SNR and instability of the electrode due to the gel used. Therefore, the present disclosure provides a facile, cost-effective, and dry graphene-based electrode to be used in a developed Arabic speller to increase the SNR.

Numerous modifications and variations of the present invention are possible in light of the above teachings. It is, therefore, to be understood that, within the scope of the appended claims, the invention may be practiced otherwise than as specifically described herein.

The invention claimed is:

1. A brain-computer interface (BCI) system, comprising:

a cap comprising a plurality of wired electrodes, wherein the wired electrodes comprises at least one electrode selected from the group consisting of a graphene-coated electrode and a reduced graphene oxide (rGO)-coated electrode, and further comprise polypyrrole that is homogenously mixed with graphene or rGO, and wherein each electrode of the wired electrodes comprises a repeating pattern of etchings, trenches or concaves that extend below a surface, and graphene and/or rGO are uniformly coated both on the surface and within the pattern;

a data acquisition and processing unit;

wherein the cap is operatively connected to the data acquisition and processing unit via the plurality of wired electrodes; and a computing device, wherein the computing device has a communications interface coupled to the data acquisition and processing unit;

wherein the BCI system removably retains the computing device;

wherein the plurality of wired electrodes is configured to detect one or more electroencephalograph (EEG) signals from a plurality of brain areas of the subject wearing the cap;

wherein the data acquisition and processing unit is configured to characterize brain activities of the subject based on the one or more EEG signals transmitted from the plurality of wired electrodes; and wherein each EEG signal of the one or more EEG signals corresponds to the brain activities of the subject.

2. The BCI system of claim 1, wherein each electrode of the wired electrodes is in the shape of a flat racket having a circular head portion and a rectangular tail portion and an average thickness in a range of 0.1 mm to 2 mm.

3. The BCI system of claim 2, wherein the circular head portion of each electrode has an average diameter in a range of 4 to 20 mm, and a repeating pattern of etched lines that are radially oriented and evenly spaced inside the circular head portion of the electrode.

4. The BCI system of claim 2, wherein the rectangular tail portion of each electrode has an average length in a range of 3 to 15 mm, an average width of 1 to 3 mm, and a series of repeating lines that extend from one edge of the rectangular tail portion to the other edge of the rectangular tail portion perpendicular to the axis of the rectangular tail portion.

5. The BCI system of claim 4, wherein the etchings, trenches or concaves have a width that is 1/10 or less than a width of the rectangular tail portion.

6. The BCI system of claim 2, wherein the circular head portion comprises the etchings, trenches or concaves in the form of 2 to 4 concentric rings.

7. The BCI system of claim 1, wherein the data acquisition and processing unit comprises a biosensing board and a dongle, and wherein the biosensing board comprises a processor and a neural interface having a plurality of channels.

8. The BCI system of claim 7, wherein the plurality of channels of the neural interface comprise Pz, P4, Cz, C4 and Fz.

9. The BCI system of claim 7, wherein each electrode of the plurality of the wired electrodes is operatively connected to each channel of the plurality of channels of the neural interface.

10. The BCI system of claim 1, wherein the polypyrrole is homogenously mixed with graphene or rGO via electrochemical polymerization from a mixture comprising pyrrole monomer and at least one selected from graphene and rGO.

11. The BCI system of claim 10, wherein the electrochemical polymerization forms a uniform coating on a conductive substrate comprising at least one polymer selected from the group consisting of polyethylene terephthalate (PET), polyacetylene, polyphenylene vinylene, polythiophene, polyaniline, and polyphenylene sulfide, wherein the conductive substrate is subsequently removed.

12. The BCI system of claim 1, wherein the wired electrodes comprise a continuous coating over entire surface of the wired electrodes.

13. The BCI system of claim 1, wherein the wired electrodes are obtained via a process comprising:

etching a substrate via laser etching, pressure embossing or mechanical surface planing to introduce the repeating pattern of the etchings, trenches or concaves and obtain a treated substrate;

coating the treated substrate with a mixture of pyrrole and graphene or graphene oxide; and polymerizing pyrrole to form the wired electrodes with a continuous coating over entire surface.

* * * * *